US012569615B2

(12) United States Patent
Demers et al.

(10) Patent No.: US 12,569,615 B2
(45) Date of Patent: Mar. 10, 2026

(54) MEDICAL DEVICE, METHOD AND SYSTEMS

(71) Applicant: DEKA Products Limited Partnership, Manchester, NH (US)

(72) Inventors: Jason A. Demers, Manchester, NH (US); Fredrick Morgan, Bedford, NH (US); Zachary Cranfield, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 403 days.

(21) Appl. No.: 17/017,162

(22) Filed: Sep. 10, 2020

(65) Prior Publication Data

US 2021/0069411 A1     Mar. 11, 2021

Related U.S. Application Data

(60) Provisional application No. 62/898,336, filed on Sep. 10, 2019.

(51) Int. Cl.
*A61M 5/142*          (2006.01)

(52) U.S. Cl.
CPC ..... *A61M 5/14248* (2013.01); *A61M 2205/18* (2013.01); *A61M 2205/3584* (2013.01); *A61M 2205/505* (2013.01); *A61M 2205/581* (2013.01); *A61M 2205/582* (2013.01); *A61M 2205/8206* (2013.01); *A61M 2205/8237* (2013.01); *A61M 2209/086* (2013.01); *A61M 2209/088* (2013.01); *A61M 2230/201* (2013.01)

(58) Field of Classification Search
CPC ..... A61M 5/14248; A61M 2005/14268; H02J 50/10
See application file for complete search history.

(56) References Cited

U.S. PATENT DOCUMENTS

| | | | |
|---|---|---|---|
| 8,414,522 B2 | 4/2013 | Kamen et al. | |
| 8,491,570 B2 | 7/2013 | Kamen et al. | |
| 8,641,672 B2 * | 2/2014 | Yodfat | A61M 5/1723 604/151 |
| 8,821,442 B2 * | 9/2014 | Haar | A61M 5/14248 320/128 |
| 8,905,972 B2 * | 12/2014 | Smith | A61M 5/14248 604/152 |

(Continued)

FOREIGN PATENT DOCUMENTS

| | | |
|---|---|---|
| CN | 101193671 | 6/2008 |
| CN | 101541360 | 9/2009 |

(Continued)

OTHER PUBLICATIONS

International Search Report and Written Opinion mailed Nov. 12, 2020, issued in PCT International Patent Application No. PCT/US2020/050174, 11 pages.

(Continued)

*Primary Examiner* — Laura A Bouchelle
(74) *Attorney, Agent, or Firm* — Reid Knott Cunningham

(57) ABSTRACT

A medical device system is disclosed. The medical system includes a medical device including a first portion and a second portion; and an accessory, wherein the accessory configured to attach to the medical device and provide battery power to the medical device.

4 Claims, 26 Drawing Sheets

(56) References Cited

U.S. PATENT DOCUMENTS

| | | | |
|---|---|---|---|
| 9,132,227 B2 | 9/2015 | Bryant, Jr. et al. | |
| 9,248,232 B2 * | 2/2016 | Yodfat | A61B 5/14532 |
| 9,656,031 B2 | 5/2017 | Mandro et al. | |
| 9,662,438 B2 | 5/2017 | Kamen et al. | |
| 9,912,174 B2 * | 3/2018 | Soar | H04B 5/0031 |
| 10,195,343 B2 | 2/2019 | Kamen et al. | |
| 10,238,794 B2 | 3/2019 | Kamen et al. | |
| 2007/0073235 A1 | 3/2007 | Estes et al. | |
| 2008/0129486 A1 | 6/2008 | Jeckelmann et al. | |
| 2009/0326445 A1 | 12/2009 | Graskov et al. | |
| 2011/0166512 A1 | 7/2011 | Both et al. | |
| 2013/0030255 A1 | 1/2013 | Embry, II | |
| 2014/0107579 A1 | 4/2014 | Lanigan et al. | |
| 2016/0158436 A1 | 6/2016 | Yang | |

FOREIGN PATENT DOCUMENTS

| | | |
|---|---|---|
| CN | 104784777 | 7/2015 |
| WO | 2013184784 | 12/2013 |

OTHER PUBLICATIONS

Preliminary Report on Patentability mailed Mar. 24, 2022, issued in PCT International Patent Application No. PCT/US2020/050174, 8 pages.

* cited by examiner

12

29

IOB    0.9U
THURSDAY
JUNE 20, 2019

LAST BOLUS

TRENDS

MENU

BOLUS

CGM: 90 mg/dL

87%          124U

MEDICAL DEVICE, METHOD AND SYSTEMS

CROSS REFERENCE TO RELATED APPLICATIONS

The present application is a Non-Provisional Application which claims priority from U.S. Provisional Patent Application Ser. No. 62/898,336, filed Sept. 10, 2019 and entitled Medical Devices, Methods and Systems, which is hereby incorporated herein by reference in its entirety.

FIELD OF THE INVENTION

This disclosure relates to medical devices. More specifically, this disclosure relates to devices, methods and systems.

BACKGROUND OF THE INVENTION

Many potentially valuable medicines or compounds, including biologicals, are not orally active due to poor absorption, hepatic metabolism or other pharmacokinetic factors. Additionally, some therapeutic compounds, although they can be orally absorbed, are sometimes required to be administered so often it is difficult for a patient to maintain the desired schedule. In these cases, parenteral delivery is often employed or could be employed.

Effective parenteral routes of drug delivery, as well as other fluids and compounds, such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compounds over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight and cost of these devices is also an ongoing challenge. Additionally, these devices often apply to the skin and pose the challenge of frequent re-location for application. Providing power to or charging of these devices can be cumbersome or problematic in certain scenarios. The small size of such devices also limits the amount of power which these devices can store and puts constraints on the size of various components included therein. Additionally, the integration of these devices into networked systems, while beneficial, has not been perfected.

SUMMARY

In accordance with one aspect of the present invention, a medical device system is disclosed. The medical system includes a medical device including a first portion and a second portion; and an accessory, wherein the accessory configured to attach to the medical device and provide battery power to the medical device.

Some embodiments of this aspect of the invention may include one or more of the following. Wherein the accessory attaches to the second portion of the medical device. Wherein the accessory attaches to the first portion of the medical device.

In accordance with one aspect of the present invention, a medical system. The medical system may comprise a medical device accessory. The medical device accessory may have a mechanical coupling. The medical device may also include at least one additional component selected from a list consisting of charging circuitry, a user interface, a wireless signal booster, and an alarm. The system may also include a medical device which engages with the mechanical coupling to removably attach to the medical device accessory.

In some embodiments, the charging circuitry may be wireless charging circuitry. In some embodiments, the charging circuitry may be a wired connection charging circuitry. In some embodiments, the user interface may include a touch screen. In some embodiments, the system may further comprise an analyte monitor. In some embodiments, the wireless signal booster may boost an analyte monitor signal output from the analyte monitor. In some embodiments, the alarm may be a vibratory motor. In some embodiments, the alarm may be at least one light emitter. In some embodiments, the alarm may be an audio speaker. In some embodiments, the medical device may include a second alarm. The alarm of the medical device accessory may be the same type of alarm as the second alarm of the medical device, but may be a more powerful or stronger version of that alarm. In some embodiments, the medical device may be a pump. In some embodiments, the medical device may be a diabetes management device. In some embodiments, the medical device may be an insulin pump.

The details of one or more embodiments are set forth in the accompanying drawings and the description below. Other features and advantages will become apparent from the description, the drawings, and the claims.

BRIEF DESCRIPTION OF THE DRAWINGS

These and other aspects will become more apparent from the following detailed description of the various embodiments of the present disclosure with reference to the drawings wherein.

Like reference symbols in the various drawings indicate like elements.

DETAILED DESCRIPTION OF THE PREFERRED EMBODIMENTS

Figure 1:
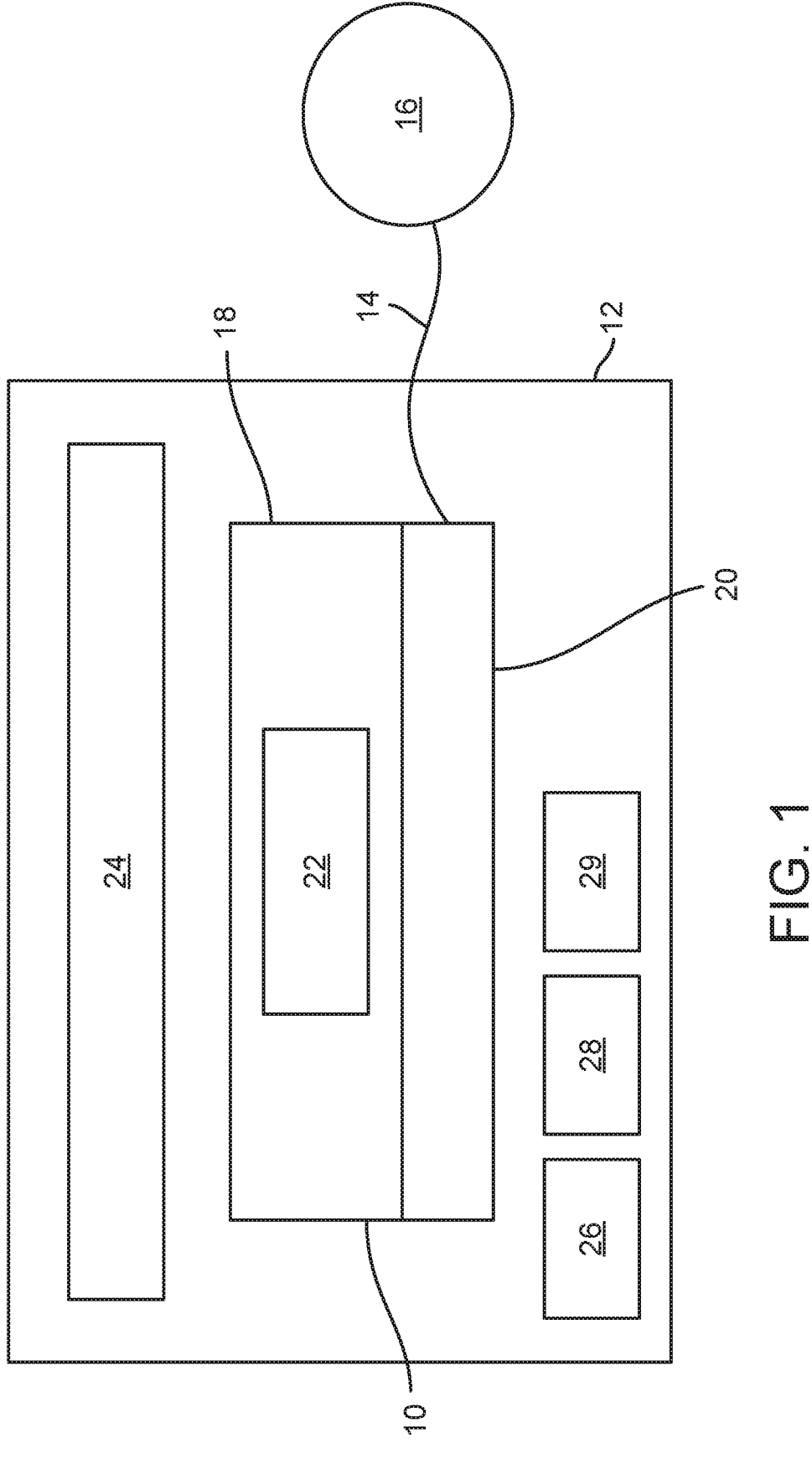
FIG. 1 depicts a block diagram of a system including a medical device and a coupled medical device accessory.
Figures 2, 3, 4, 5:
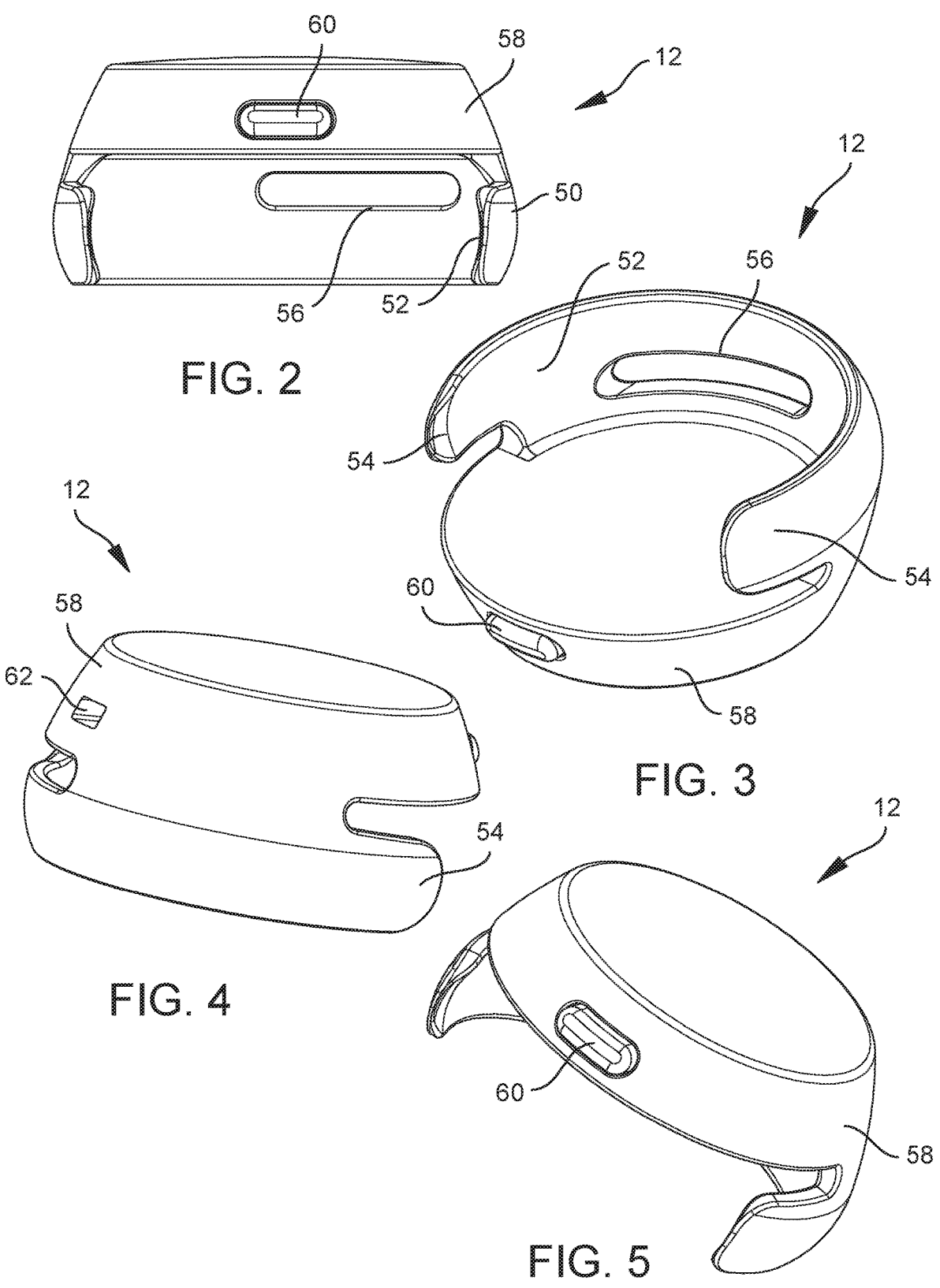
FIGS. 2-7 depict an embodiment of a medical device accessory.

FIG. 1 depicts a block diagram of a medical device 10 and coupled accessory 12. The medical device 10 may be any medical device including, but not limited to, ambulatory medical devices, drug delivery devices, physiological monitors, analyte sensors, diabetes management devices, and medical devices intended for use in a home or other non-clinical/non-hospital setting. A single accessory 12 may also be coupled to multiple medical devices 10 (e.g. an insulin pump and glucose meter). The block diagram shown in FIG. 1 depicts the medical device 10 as a drug delivery device which is in fluid communication via tubing 14 with a patient access 16 such as, for example, a needle, cannula, or subcutaneous infusion set. The medical device 10 may deliver a drug or drugs such as insulin, glucagon, treprostinil, an oncology drug, etc., or some combination thereof to the patient.

The medical device 10 is depicted as having a first portion 18 and second portion 20. The second portion 20 may be a cartridge or other consumable including a drug reservoir and perhaps valve and/or acutatable pumping components which mates to the first portion 18. The first portion 18 may include a controller, battery 22, pump actuation assembly, sensors, communication hardware, and other reusable components. An example of such a drug delivery device and/or the medical device having a first portion and a second portion are shown and described in U.S. patent application Ser. No. 13/788,260, filed Mar. 7, 2013 and entitled Infusion Pump Assembly, now U.S. Publication No. US-2014-0107579, published Apr. 17, 2014; U.S. Pat. No. 8,491,570, issued Jul. 23, 2013 and entitled Infusion Pump Assembly; and U.S. Pat. No. 8,414,522, issued Apr. 9, 2013 and entitled Fluid Delivery Systems and Methods, each of which is incorporated herein by reference in its entirety. Though various embodiments of this disclosure are described in relation to particular medical devices 10 such as drug delivery devices or diabetes management devices, this is done for illustrative purposes and other medical devices 10 may be used in place of the example medical devices 10 described.

An accessory 12 may be coupled the medical device 10 electrically, communicatively, mechanically or some combination thereof. Where an accessory 12 is coupled to multiple medical devices 10, the type of coupling(s) between the medical devices 10 and the accessory 12 may differ. For example, a first medical device may be electrically, communicatively, and mechanically coupled to the accessory 12, while a second medical device may only be communicatively coupled.

The accessory 12 may cooperate with the medical device 10 to aid in providing power to the medical device 10, augment existing functionality of the medical device 10, and/or provide additionally functionality. For example, the accessory 12 may include a power source such as a battery 24. This battery 24 may be used as an auxiliary battery which may be drawn from in place of the battery 22 included in the medical device 10. The battery 24 included in the accessory 12 may also be used to recharge the battery 22 included in the medical device 10. In such instances, a contact based electrical connection between the accessory 12 and medical device 10 may be used to transmit power. Such embodiments may include a set of conductive contacts which may cooperate with contacts provided on the medical device 10 when the accessory 12 is installed on the medical device 10. A male/female plug type interface may also be included on the accessory 12 and medical device 10 to provide electrical communication. Alternatively, the battery 22 of the medical device 10 may be recharged via a wireless coupling. The accessory 12 may be wirelessly (e.g. inductively, acoustically) coupled to the medical device 10 and transfer power to the medical device 10 using, for example, but not limited to a PMA, Airfuel, A4WP, Open dots, Rezence, Qi, acoustic power transfer or other wireless power transfer standard. This may, for example, allow for a user to travel or perform various activities with the medical device 10 without needing to carry a supply of relatively heavy consumable batteries or various adapters and cabling. Moreover, a user may be able to charge the medical device 10 in scenarios when access to an electrical grid is not available or inconvenient (e.g. camping, hiking, beach, etc.). Additionally, it may facilitate recharging of a medical device 10 while the medical device 10 is currently in use and attached to the patient. An insulin pump, for example, may be recharged by a user wearing the pump while sleeping via the installed accessory 12. The absence of cords may be beneficial/desirable for many reasons, including, but not limited to, making the experience more hassle free, convenient, and user-friendly. Additionally, concerns related to damage of cords or charging ports may be eliminated. Wireless charging may also simplify certain aspects of medical device 10 design as it may, for example, increase the ease of water-proofing such devices.

An accessory 12 may include one or more of alarm 26. The alarm 26 may include a speaker, tactile stimulation arrangement (e.g. vibratory motor), illuminator, or any combination of one or more thereof. In some embodiments, the alarm 26 may augment an existing alarm system included in the medical device 10. As the accessory 12, in some embodiments, may have its own dedicated battery 24, the accessory 12 may be configured to issue stronger or more aggressive alarms than an alarm system included in the medical device 10. For example, a larger or more powerful vibratory motor may be included in the accessory 12 than would be practical to include in the medical device 10. Similarly, a larger or louder speaker may be included in the accessory 12. An illuminator included as part of the alarm 26 of the accessory 12 may have a higher lumen output than any lights included as part of the medical device 10. Such alarms may, for example, aid in awakening a user or caregiver during sleep.

This may be particularly advantageous for insulin pump users as awakening response may be impaired during excursions into nocturnal hypoglycemia. In some embodiments, an accessory 12 may include a thermal alarm which may have one or more heating element. The accessory 12 may, for example, generate heat with the heating element which may alert a user that an alarm state or condition of interest is in existence. The heat produced may be 5° F. or more above body temperature so as to be noticeable, but not excessive.

The accessory 12 may include a wireless communicator 28. The wireless communicator 28 may include one or more of a cellular, WiFi, Bluetooth, Zigbee, etc. antenna. The wireless communicator 28 may allow for the accessory 12 to download updates for the medical device 10. The wireless communicator 28 may provide wireless communications capability for medical devices 10 which do not have such capability. Additionally, the wireless communicator 28 may serve to supplement existing communicators in a medical device 10. For example, the wireless communicator in the accessory 12 may have a greater range or transmitted power output than a communicator or communicators included in the medical device 10. The accessory 12 may be communicatively coupled to the medical device 10 and may boost any signals output from the medical device 10 or act as a repeater for signals output from the medical device 10. This may allow for the medical device 10 to have an increased communication range or be less susceptible to obstructions which may limit robustness of communication connections to other components of a medical system. For example, the accessory 12 may output a stronger signal allowing for remote monitoring of medical device 10 status. In one embodiment, the wireless communicator 28 of the accessory 12 may receive data from a physiological or analyte sensor and wirelessly transmit the data to a receiver at a frequency or signal strength which would be impractical if one were to rely solely on a battery 22 included in the medical device 10. This may be particularly advantageous for certain medical devices 10 such as continuous glucose monitors which are worn during sleeping hours. As the user may shift position and move the monitor into a position in which the signal it outputs is obstructed, signal dropout presents an issue. Alarms related to dropout during sleep can be disruptive to a user, lower quality of life, and may play a significant role in decisions of patients to discontinue use of such monitors despite the benefits they provide. Additionally, such signal issues may lead to missed blood glucose data points on a remote monitoring device (e.g. smartphone or dedicated monitor). A wireless communicator 28 in a coupled accessory 12 may aid in mitigating these issues.

The accessory 12 may include a user interface 29. The user interface 29 may include hard buttons which are user actuated. When actuated, such buttons may, for example, cause inputs to be provided to buttons on the medical device 10. This may allow for a user to maintain full functionality of a medical device 10 in the event that placement of the accessory 12 on the medical device 10 covers one or more button of the medical device 10. Hard buttons may also have their own functionalities unrelated to buttons included on a medical device 10. Such buttons may, for example, aid in navigation through various screen flows displayed on a user interface 29 including a display (see, e.g. FIG. 77). Such a display may be a liquid crystal display, LED display, OLED display, plasma display, touch screen display, or any other suitable display. In such embodiments, the accessory 12 may allow for a medical device 10 to be provided with large and/or bright display having significant power demands as the accessory 12 may have its own battery 24. Thus, the accessory 12 may provide the user an aesthetically pleasing and easy to use graphical user interface which may convey information about the medical device 10, current therapy, or patient related data. The accessory 12 may also allow for programming or modification of a therapy to be provided by the medical device 10. The accessory 12 may thus replace or provide redundancy to a user interface on a smart phone or similar device used to review and set therapy parameters and/or check analyte levels or trends.

In some embodiments, an accessory 12 may also allow for user customization of the appearance of the medical device 10. For example, the accessory 12 may have a removable skin which forms part of the housing 50 (see, e.g. FIGS. 2-5) of the accessory 12. A number of different skins may be attached to the accessory 12 depending on user preference. Thus, the user may modify the aesthetics of the medical device 10 to suit their particular taste. Alternatively, the appearance may be modified to make the accessory 12 readily distinguishable from other accessories 12. The removable skin may be coupled to the accessory 12 in any suitable manner.

For example, a magnetic coupling or snap fit may be used or an adhesive may be used to adhere the skin to the accessory 12. The skin may also be coupled to the accessory 12 via a clip on engagement.

Referring now to FIGS. 2-5 a number of views of an example accessory 12 are shown. The accessory 12 includes a housing 50. The housing 50 includes a medical device receiver which is shown as a bay 52 that is sized and shaped to receive and retain a medical device 10 or portion thereof. In the example embodiment, the bay 52 includes coupling members which are depicted as arms 54 located on opposing sides of a docking opening in the housing 50. The arms 54 may be cantilevered so as to resiliently deflect outward as the medical device 10 is docked into the bay 52. A portion of the medical device 10 which is wider than a distance between the interior faces of the arms 54 in the resting state may be passed through the arms 54 and into the bay 52 while the arms 54 are deflected outwards. The arms 54 may then restore to a resting state once the medical device 10 is in place within the bay 52. Thus, the arms 54 may clip onto the medical device 10 mechanically retaining the accessory 12 in place on the medical device 10. Preferably, the resiliency of the arms 54 is chosen to allow retention of the medical device 10 under some jostling, but also to allow for installation and removal of the medical device without excessive force or effort. The housing 50 may include one or more fenestration 56 which may allow for a user to view or access a portion of the medical device 10. Fenestrations 56 may for example be included to allow a line of sight to user interface components of the medical device 10 such as indicators (e.g. lights) and/or user input components of the medical device (e.g. a touchscreen or buttons such as a bolus button on a diabetes management pump). Fenestrations 56 may also allow a user to access a portion of the medical device 10 to press against in order to remove the medical device 10 from the accessory 12.

The housing 50 may also include a second portion 58. The second portion 58 may contain one or more of, for example, a battery 24, charging circuitry, a controller (e.g. microprocessor, PLC, FPGA, etc.), memory, alarm 26, a wireless communicator 28, and a user interface 29. As shown, the accessory 12 also includes a button 60. The button 60 may turn the accessory 12 on and off. The button 60 may also be used to convey user input to accessory 12. For example, the button 60 may be used to acknowledge and silence (e.g. stop producing one or more of an audible, tactile, or visual output) or temporarily snooze an alarm being generated by the accessory 12. The accessory 12 may further include a port 62. The port 62 may be used for data (e.g. log transfer or medical device updates) or power communication. For example, the port 62 may be used to charge the battery 24 included in the accessory 12. Any suitable port 62 may be used such as a USB, mini-USB, micro-USB, barrel jack, or any proprietary connector port. In alternative embodiments, no port 62 may be included. Instead, a battery 24 of the accessory 12 may be wirelessly charged by a charging mat, platform, stand, or similar item. Where embodiments of accessories 12 are shown herein as port 62 free or having a particular port 62 type, it should be understood that this is merely exemplary. Any type of port may be used on any of the embodiments depicted herein and any of the embodiments herein may be wirelessly charged. Likewise, any embodiment herein may include a charging port, but also be capable of wireless charging.

Figures 6, 7:
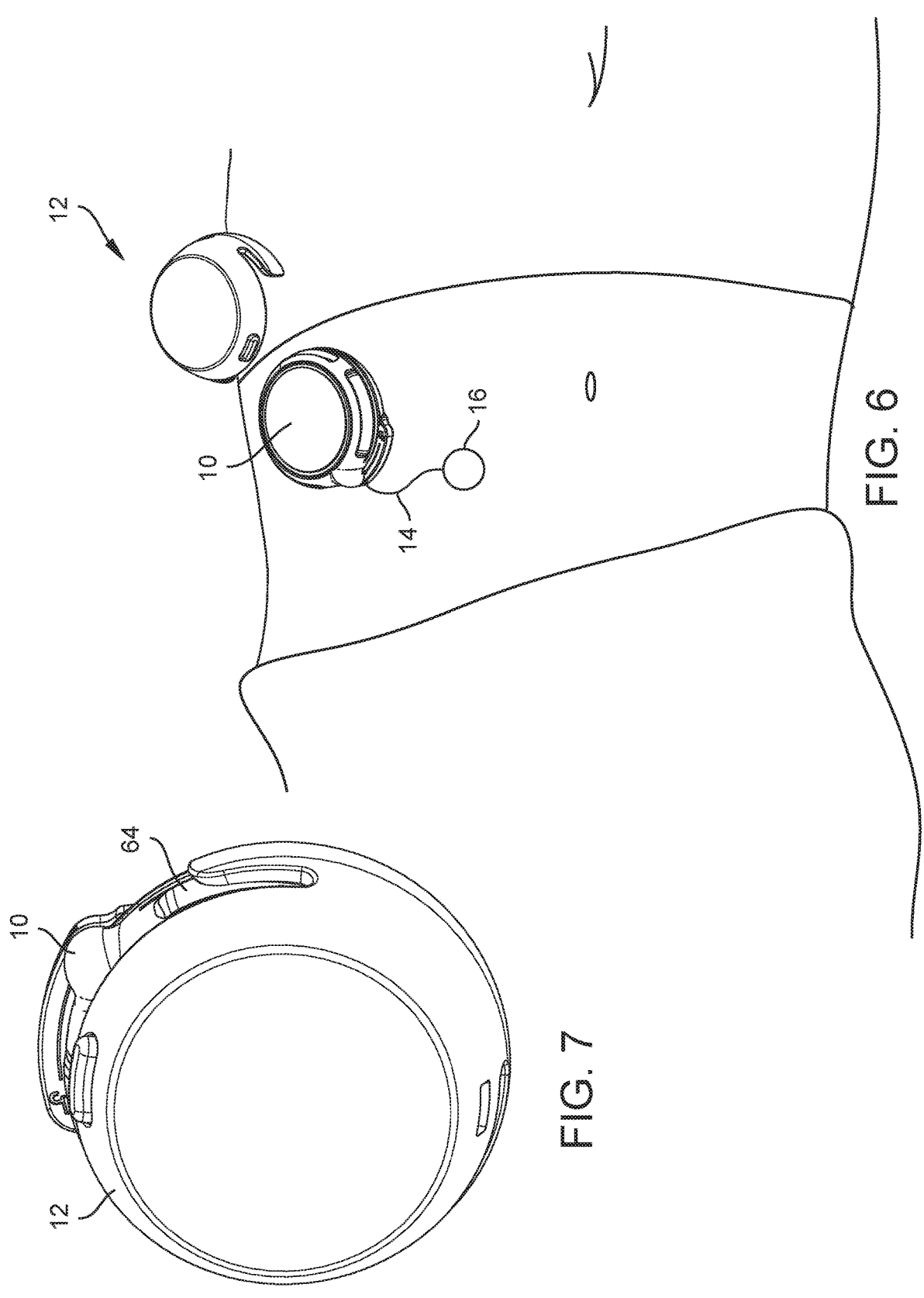

Referring now to also FIGS. 6 and 7, the accessory 12 is respectively depicted with a medical device 10 retained therein and with a medical device 10 about to be docked thereto. As shown best in FIG. 6, the medical device 10 may be a drug delivery device such as an ambulatory infusion pump. The medical device 10 may be attached via tubing 14 to an infusion set 16 (as shown) or may be a patch type drug delivery device. The medical device 10 may be retained on the body with a skin compatible adhesive. The accessory 12 may be attached to the medical device 10 while the medical device 10 remains in situ on the user. Preferably, any edges of the accessory 12 which may be adjacent to the skin of a patient when clipped on a medical device 10 in situ are rounded or blunted so as to be comfortable for a patient wearing the medical device 10. As shown in FIGS. 6 and 7, the footprint of at least one medical device receiving portion of the housing 50 for the accessory 12 may mimic the footprint of the medical device 10. In the example embodiment, the medical device 10 is depicted as a disc like device and the bay 52 of the accessory has a complimentary footprint. Other footprints for medical devices 10 and bays 52 are also possible such as various polygonal shapes (e.g. rectangular), round shapes, obrounds, or other shapes with both rounded and straight line features. When retained on the medical device 10 the arms of the accessory 12 may clip around an edge 64 of the medical device 10.

Figure 8:
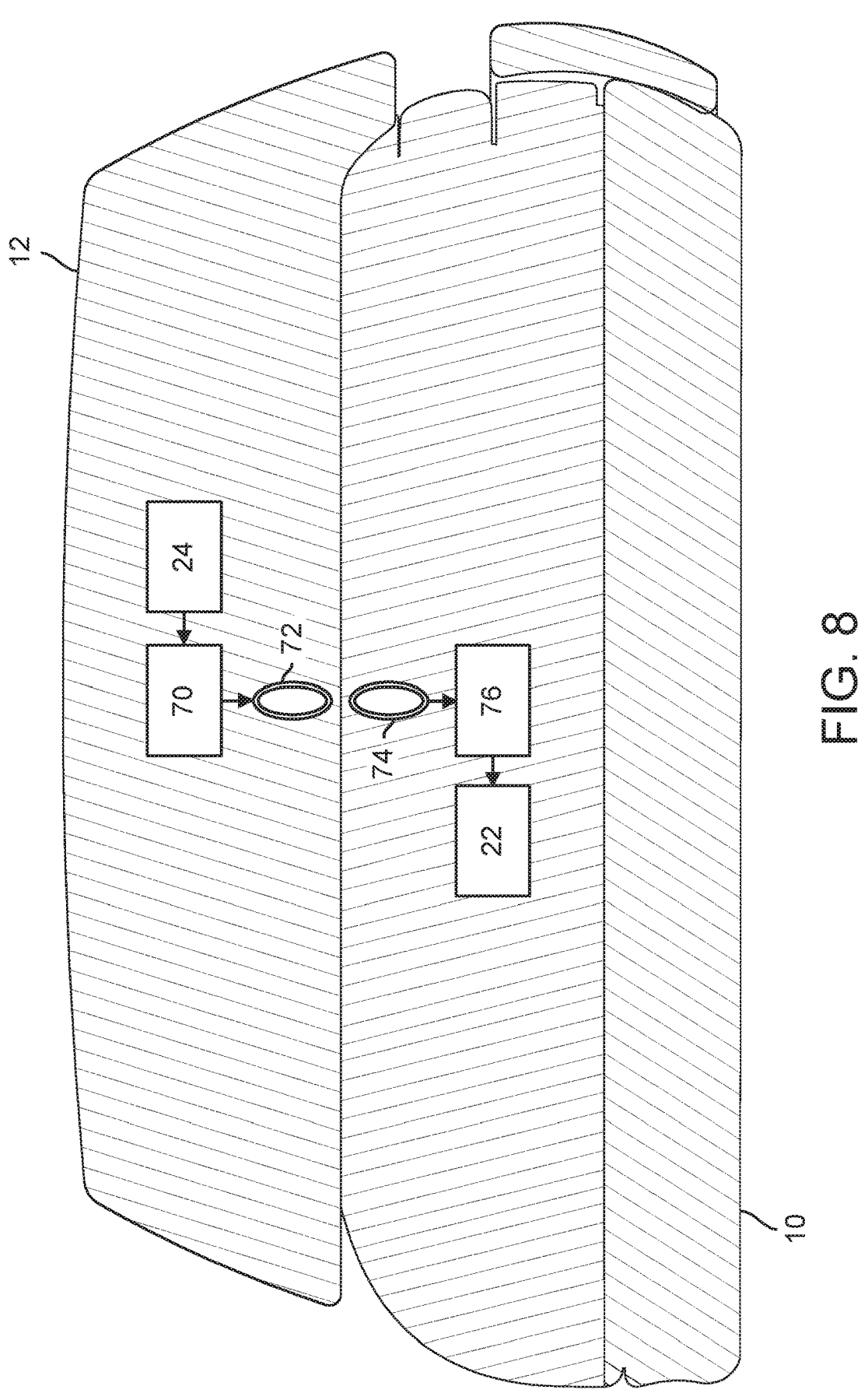
FIG. 8 depicts a block diagram shown charging components included in a medical device and medical device accessory.
Figures 9, 10, 11, 12:
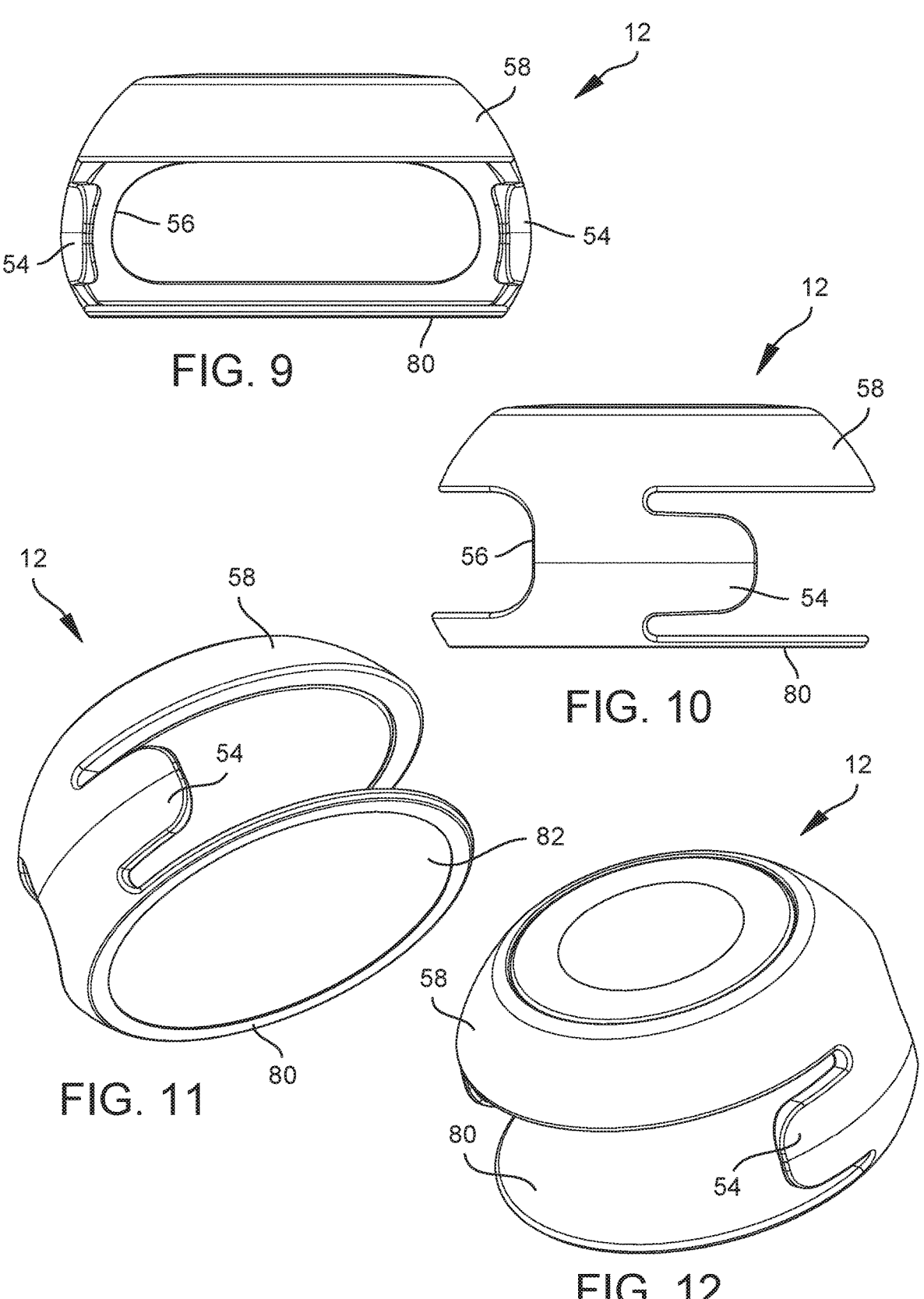
FIGS. 9-12 depict another embodiment of a medical device accessory.

Referring now also to FIG. 8, a cross-sectional view of the accessory 12 shown in FIG. 2-7 retained on a medical device 10 is shown. For sake of illustration, only the power transfer components of the accessory 12 and medical device 10 are shown and are depicted in block diagram form. As shown, the accessory 12 includes a DC power source which is shown as a battery 24. The accessory 12 may also include a transmitter circuit 70 which may include an inverter for providing AC to a transmitting coil 72 also included in the accessory 12. The medical device 10 may include a corresponding receiver coil 74. The receiver coil 74 may be in electrical communication with receiver circuit 76 which may include a rectifier. The receiving circuit 76 may output direct current to a rechargeable battery 22 of the medical device 10 to charge the battery 22.

Another embodiment of an exemplary accessory 12 is depicted in FIGS. 9-12. As shown, the housing 50 includes a first portion medical device receiver which is formed as a pocket. The pocket is defined by arms 54 which serve as coupling members for retaining the accessory 12 in place on the medical device 10. The pocket is also defined by the second portion 58 (which may be furnished similarly to as described with respect to FIGS. 2-8) of the housing 50 and a base plate 80. The example embodiment also includes a fenestration 56, though additional fenestrations 56 may be included in alternative embodiments. The base plate 80 may allow for the medical device 10 to be surrounded at least partially on all sides. Thus the medical device 10 may be attached to the accessory 12 when removed from the body. In some embodiments, a bottom face of the base plate 80 may include an adhesive region 82 upon which a skin compatible adhesive may be applied. Thus the accessory 12 may be adhered to the patient with the medical device 10 retained therein.

In some embodiments, the charge rate of the medical device 10 may be altered as the medical device 10 is charged. For example, the medical device 10 may be rapidly charged by the accessory 12 until the battery level of the medical device 10 reaches a certain level. For example, the medical device 10 may be rapidly recharged until the battery 22 of the medical device 10 reaches a percentage (e.g. 50% or greater) where the medical device 10 will be capable of functioning for a predefined period of time. This may allow a user to quickly dock the accessory 12 to the medical device 10 to reach an acceptable charge state while minimizing any disruption to activities the patient is taking part in. The medical device 10 may be charged to a full state when it is more convenient for the user. Thus, convenience may be maximized without unnecessarily degrading the battery 22. In some embodiments, the accessory 12 may only rapidly recharge the battery 22 of the medical device 10 upon receipt of a communication from the medical device 10 that the battery 22 included in the medical device 10 is amenable to a rapid recharging (of appropriate type and has no related errors or faults).

Figures 13, 14, 15, 16:
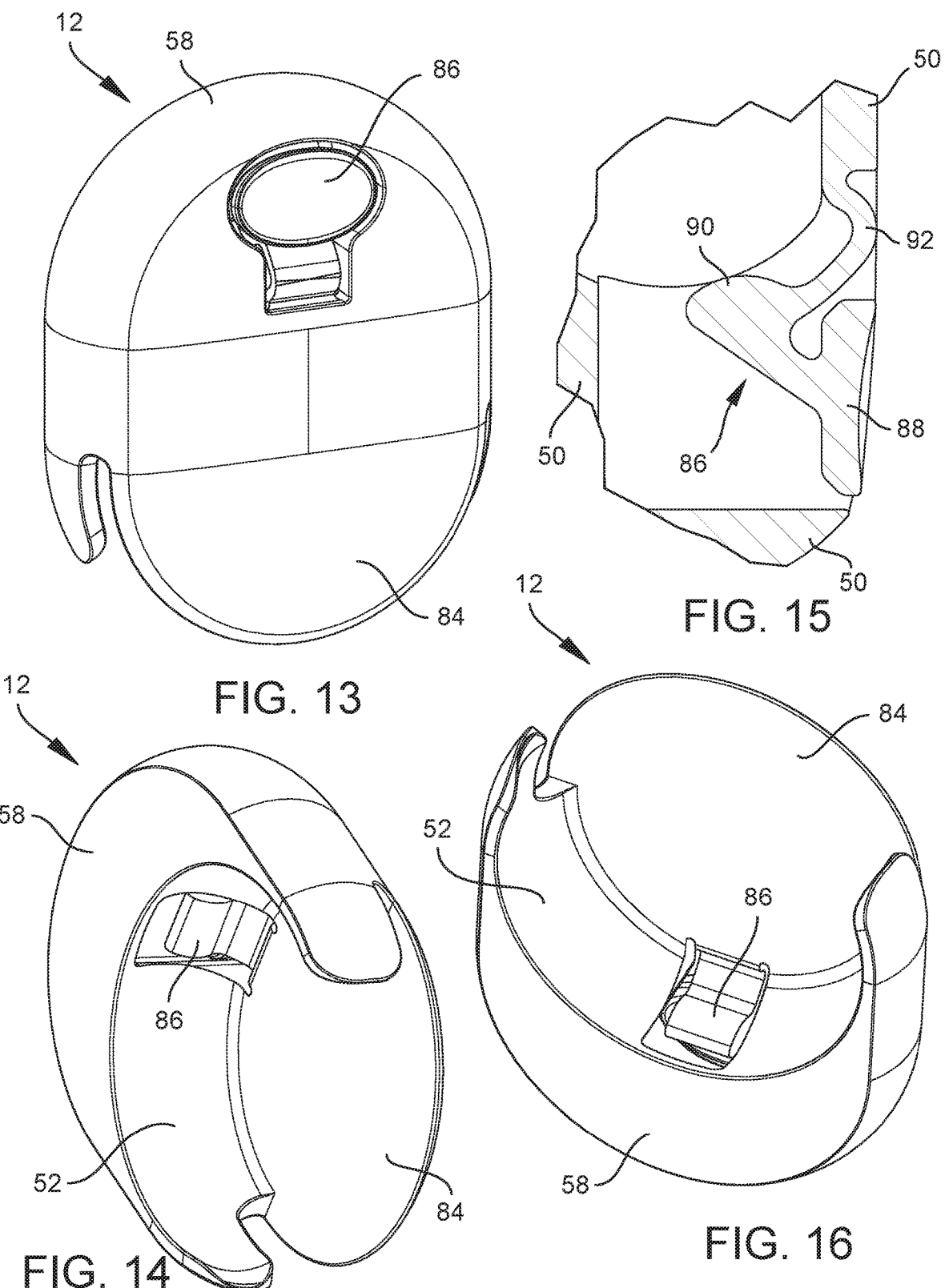
FIGS. 13-16 depict another embodiment of a medical device accessory.
Figures 17, 18, 19, 20:
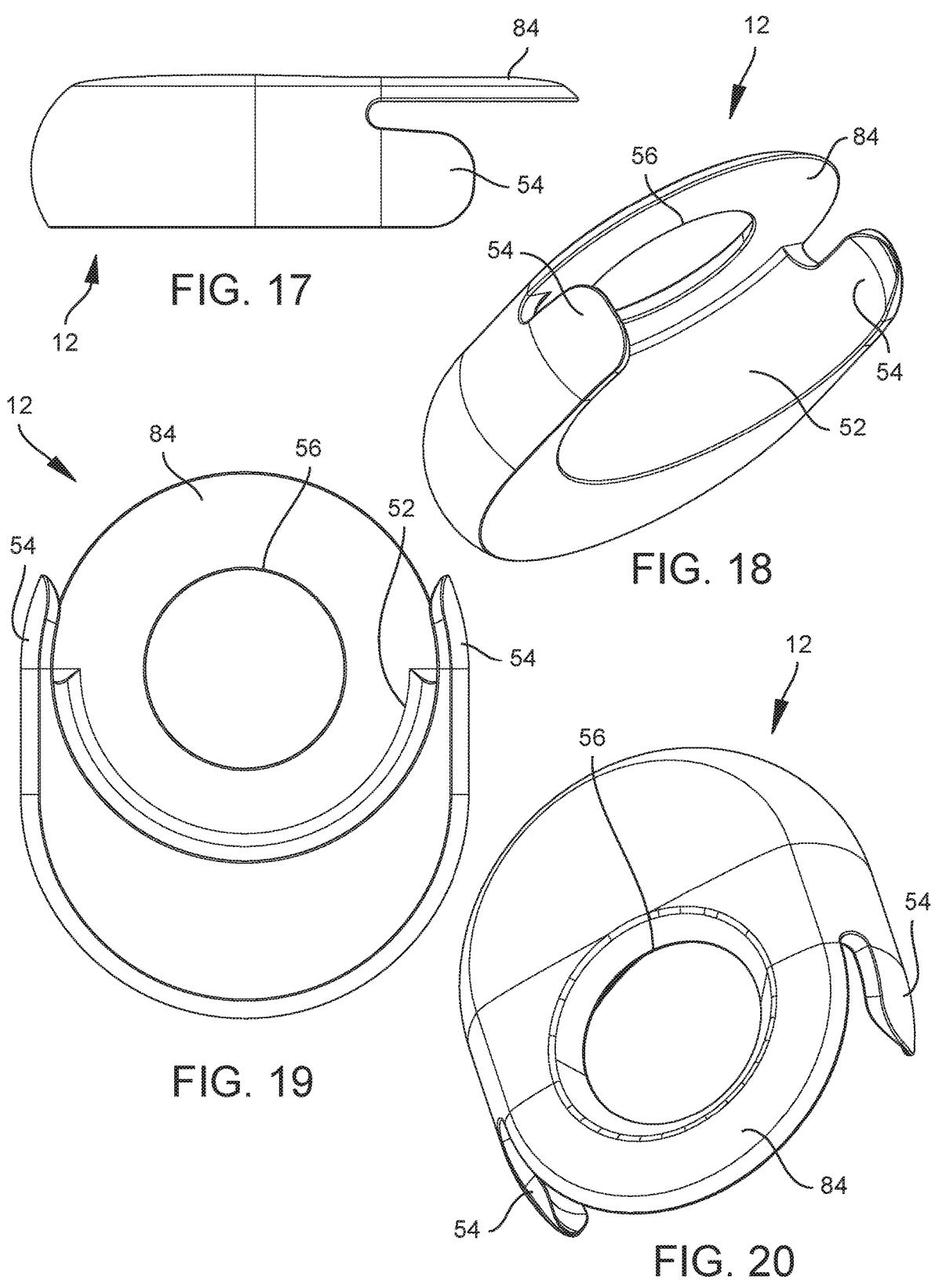
FIGS. 17-20 depict another embodiment of a medical device accessory.
Figures 21, 22, 23, 24:
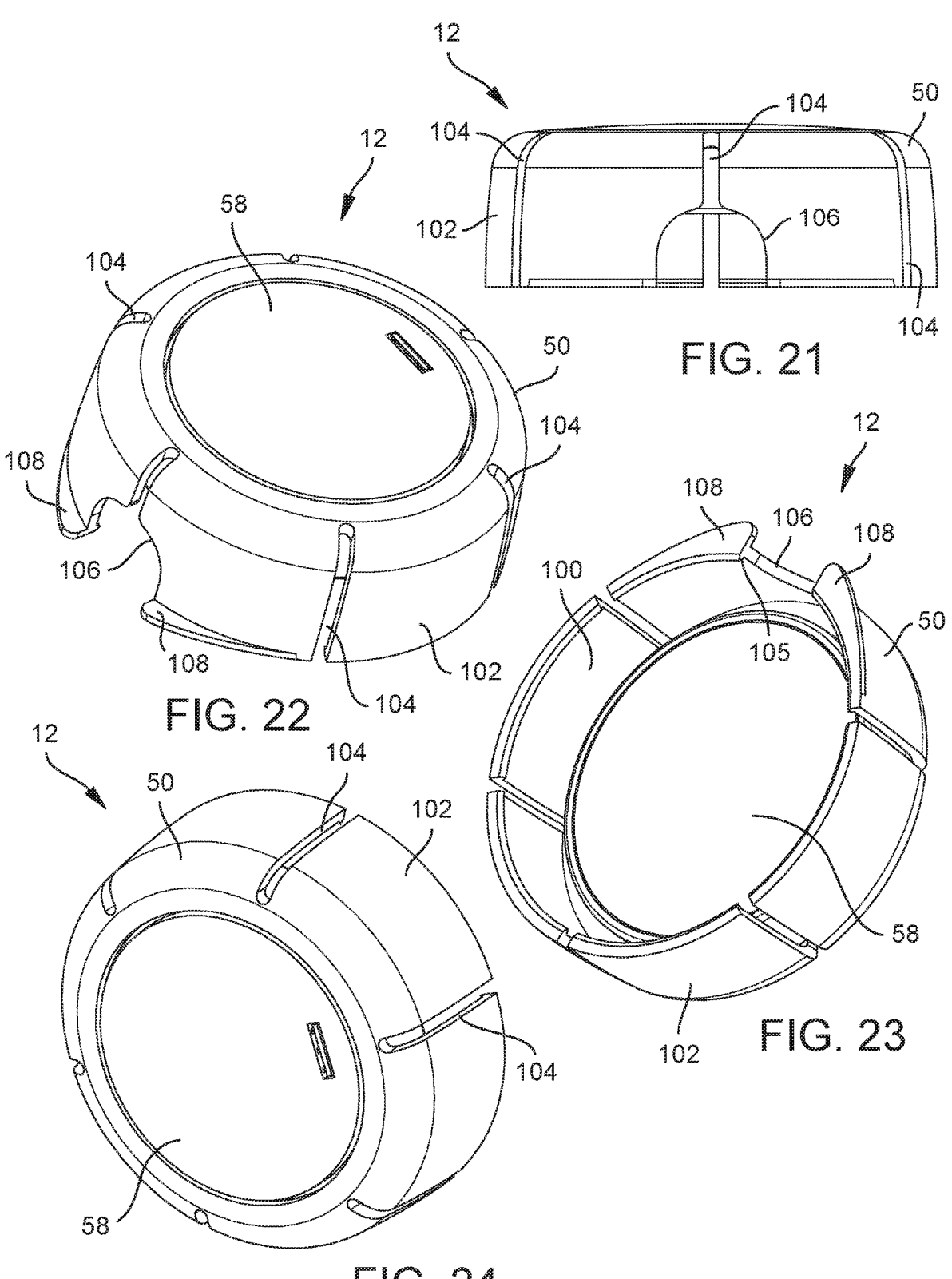
FIGS. 21-26 depict yet another embodiment of a medical device accessory.

Another embodiment of an exemplary accessory 12 is depicted in FIGS. 13-15. As shown, the housing 50 includes a bay 52 that is sized and shaped to receive and retain a medical device 10 or portion thereof. In the example embodiment, the bay 52 includes coupling members which are depicted as arms 54 located on opposing sides of a docking opening in the housing 50. The bay 52 is also defined by a top plate 84. The accessory 12 may be retained on a medical device 10 in situ. In the example embodiment, the accessory 12 includes a second portion 58. The second portion 58 is disposed laterally to the bay 52 giving the accessory 12 a profile that is only slightly taller than a medical device 10 retained therein. The second portion 58 may include components such as those described in relation to FIGS. 2-8. The example accessory 12 also includes a release mechanism 86 which may be actuated by a user to detach the accessory 12 from the medical device 10. In the example embodiment, the release mechanism 86 includes a user displaceable button which may drive an extraction finger 90 (see, e.g., FIG. 15) into the medical device 10 when the button is displaced. As best shown in FIG. 15, the release mechanism 86 may include a user contact face 88. The user contact face 88 may include a curved depression which serves as a pressing surface for a user's finger. The release mechanism 86 may also include a hinge 92 which connects the release mechanism 86 to the housing 50 of the accessory 12. In the example, the hinge 92 is depicted as a living hinge though a hinge including a pivot pin about which the release mechanism 86 may displace may be used in alternative embodiments. When depressed, the release mechanism 86 may pivot about the hinge 92 and the extraction finger 90 may exert a force against the medical device 10. This force may aid in displacing the medical device 10 out of clipping engagement with the arms 54 of the accessory 12 so that the accessory 12 may be removed from the medical device 10.

While the example accessory 12 includes a release mechanism 86, other embodiments may include similar user actuatable components which may be operated to register user inputs to the medical device 10. Thus, an accessory 12 may include a user interface 29. For example, in some embodiments, a user input mechanism may be included in an accessory 12. The user input mechanism may be a hinged displaceable component similar to the release mechanism described above. A user input mechanism may include an input finger instead of an extraction finger. Such an input finger may align with a button or the like included in a medical device 10 retained within the accessory 12. When the user input mechanism is actuated (e.g. by a user's finger) the input finger may be advanced against the input means included on the medical device 10. This may allow for the accessory 12 to be made without fenestrations 56 (see, e.g. FIG. 2-5), while still allowing operation of buttons covered by the accessory 12 when the accessory 12 is installed on the medical device 10.

Referring now to FIGS. 17-20 another exemplary embodiment of an accessory 12 is depicted. As shown, the housing 50 includes a bay 52 that is sized and shaped to receive and retain a medical device 10 or portion thereof. In the example embodiment, the bay 52 includes coupling members which are depicted as arms 54 located on opposing sides of a docking opening in the housing 50. The bay 52 is also defined by a top plate 84. The accessory 12 may be retained on a medical device 10 in situ. In the example embodiment, the accessory 12 includes a second portion 58. The second portion 58 is disposed laterally to the bay 52 giving the accessory a profile that is only slightly taller than a medical device 10 retained therein. The second portion 58 may include components such as those described in relation to FIGS. 2-8. As shown, the top plate 84 includes a fenestration 56.

Referring now to FIGS. 21-26 another exemplary embodiment of an accessory 12 is depicted. As shown, the housing 50 is cap like and includes a medical device receiver in the form of a cavity 100 that is sized and shaped to receive and retain a medical device 10 or portion thereof. The accessory 12 also includes a second portion 58 which may include the components described above in relation to FIGS. 2-8. In the example embodiment, the housing 50 includes a peripheral wall 102 which substantially surrounds the medical device 10 when retained on the medical device 10. The peripheral wall 102 may also include a lip 105 at an edge thereof which may aid in retention of the accessory 12 on the medical device 10. In some embodiments, the lip 105 may be sized to interface with a corresponding groove in a medical device 10. The peripheral wall 102 includes a number of breaks 104. These breaks 104 in the example embodiment are spaced at regular angular intervals in the peripheral wall 102. In the example, breaks 104 are included about every 60°. In alternative embodiments, breaks 104 may be included every 45-120° for example. Breaks 104 may also be irregularly spaced. In embodiments where the accessory 12 does not have a round footprint, there may, for example, be at least one break per side of the peripheral wall 102 of the accessory 12. In the example embodiment, the breaks 104 follow a straight line path generally parallel to the height axis of the accessory 12 and are cut into the peripheral wall 102 in a direction that is substantially perpendicular to the height axis of the accessory 12. It should be appreciated that as used herein, the term "cut" may, but does not necessarily mean that a feature is formed via a material removal process. Features described as cut out, cut into, etc. a component may be formed during molding, casting, a material additive process (e.g. 3D printing), or other manufacturing process without removal of material from the component. In other embodiments, the path of the breaks 104 need not follow a straight line path and may be cut into the peripheral wall 120 at other angles than that shown.

Figures 25, 26:
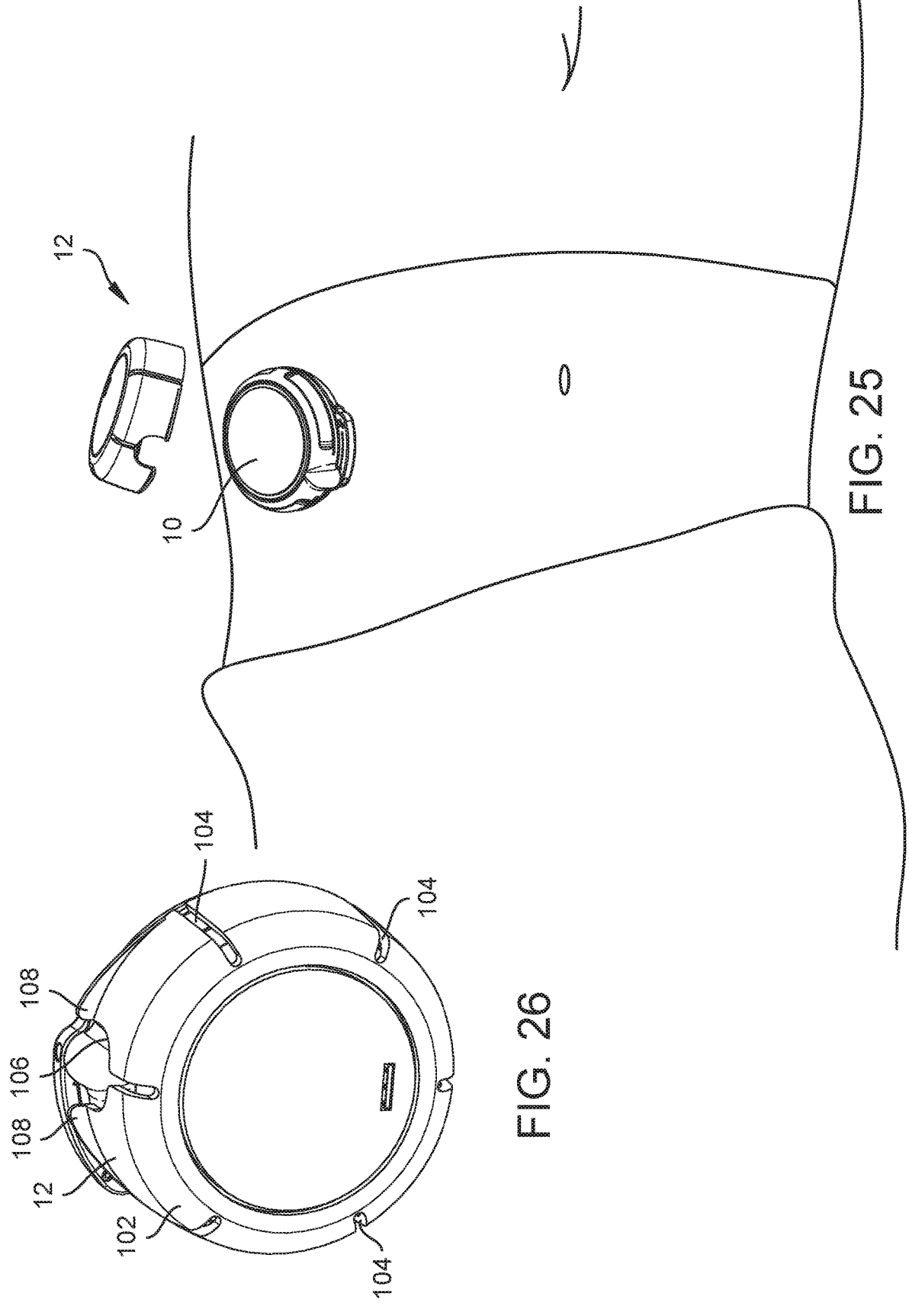
Figures 27, 28, 29, 30:
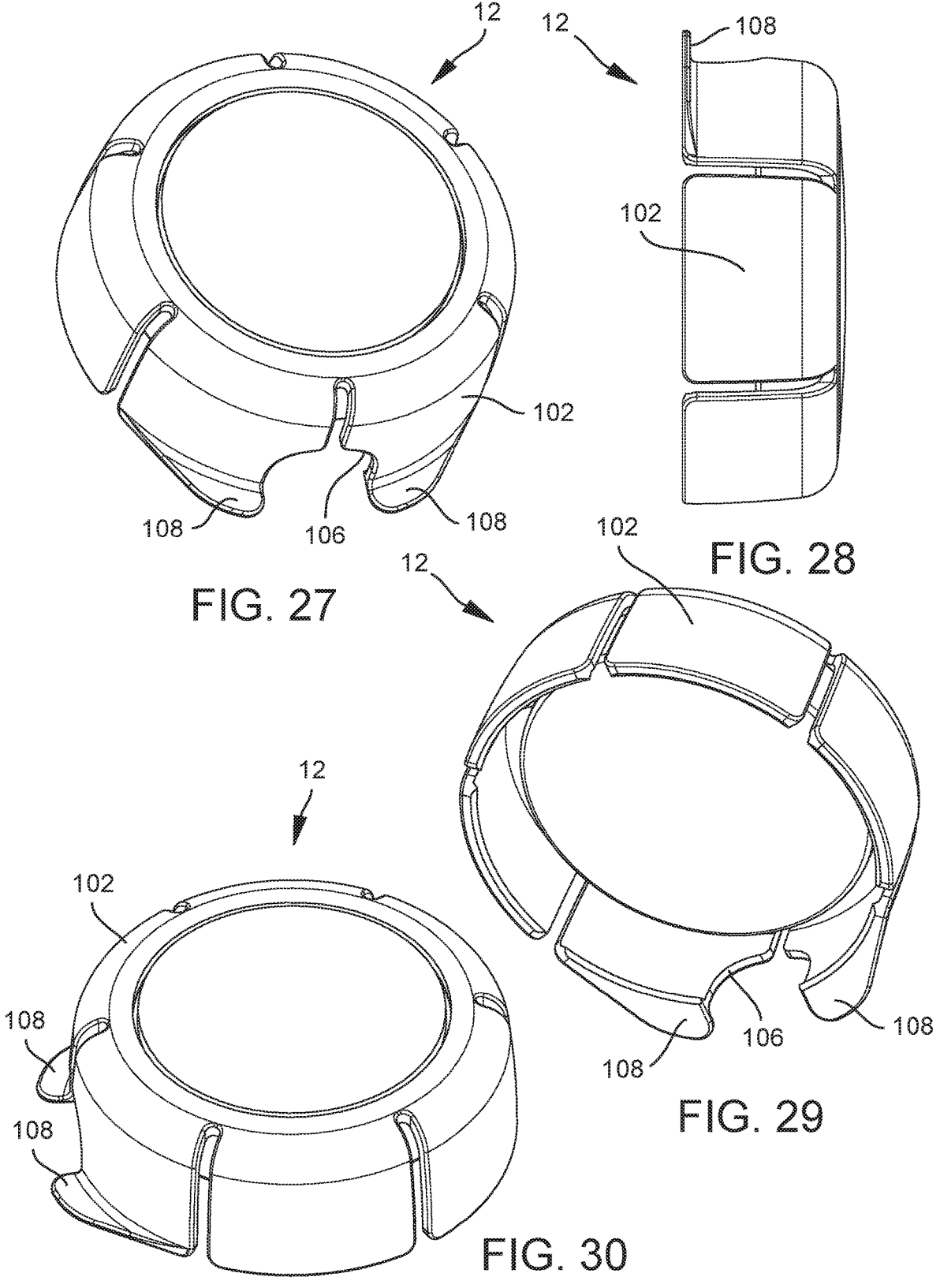
FIGS. 27-30 depict yet another embodiment of a medical device accessory.
Figures 31, 32, 33, 34:
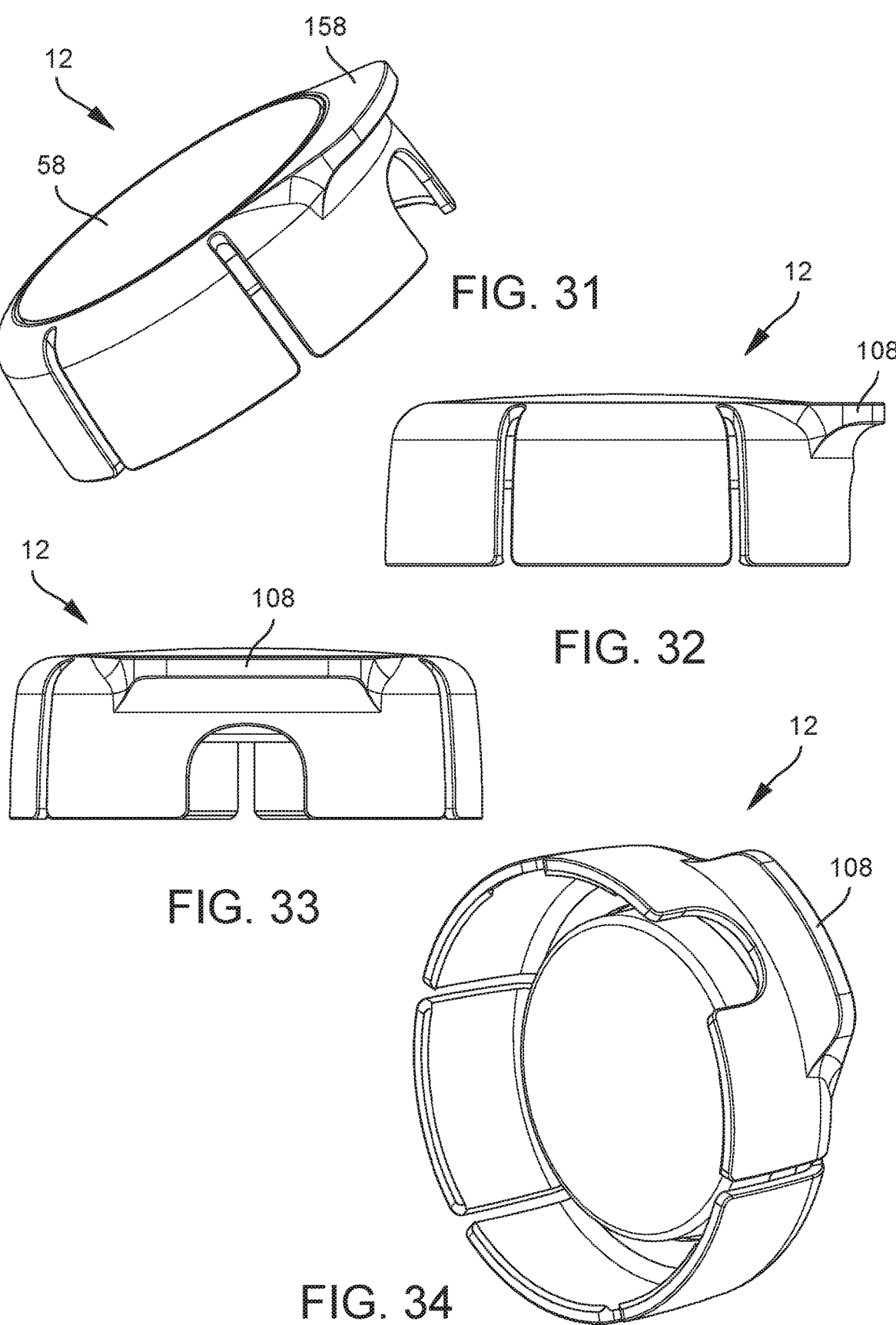
FIGS. 31-34 depict yet another embodiment of a medical device accessory.
Figures 35, 36, 37, 38:
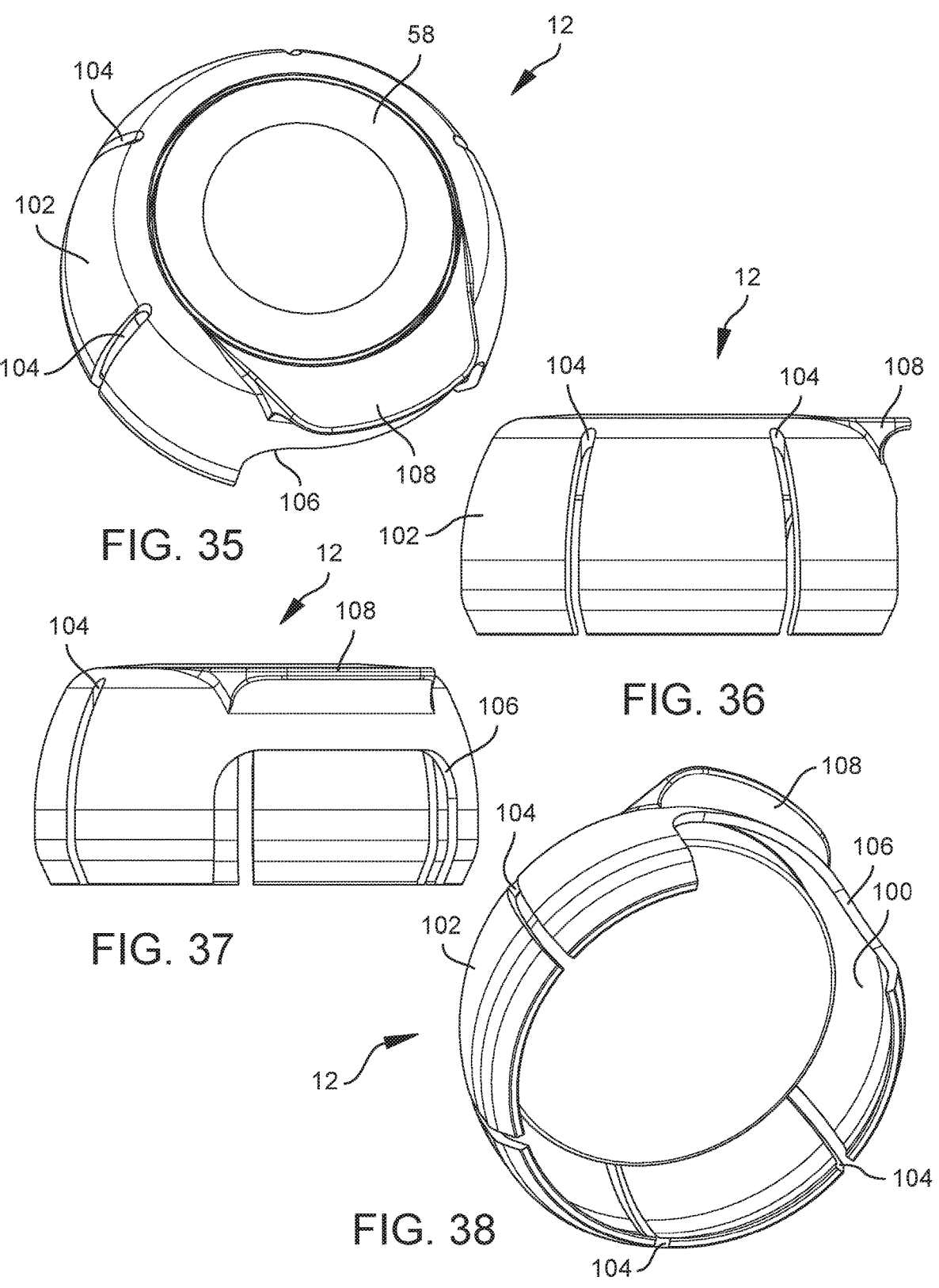
FIGS. 35-40 depict yet another embodiment of a medical device accessory.
Figures 39, 40:
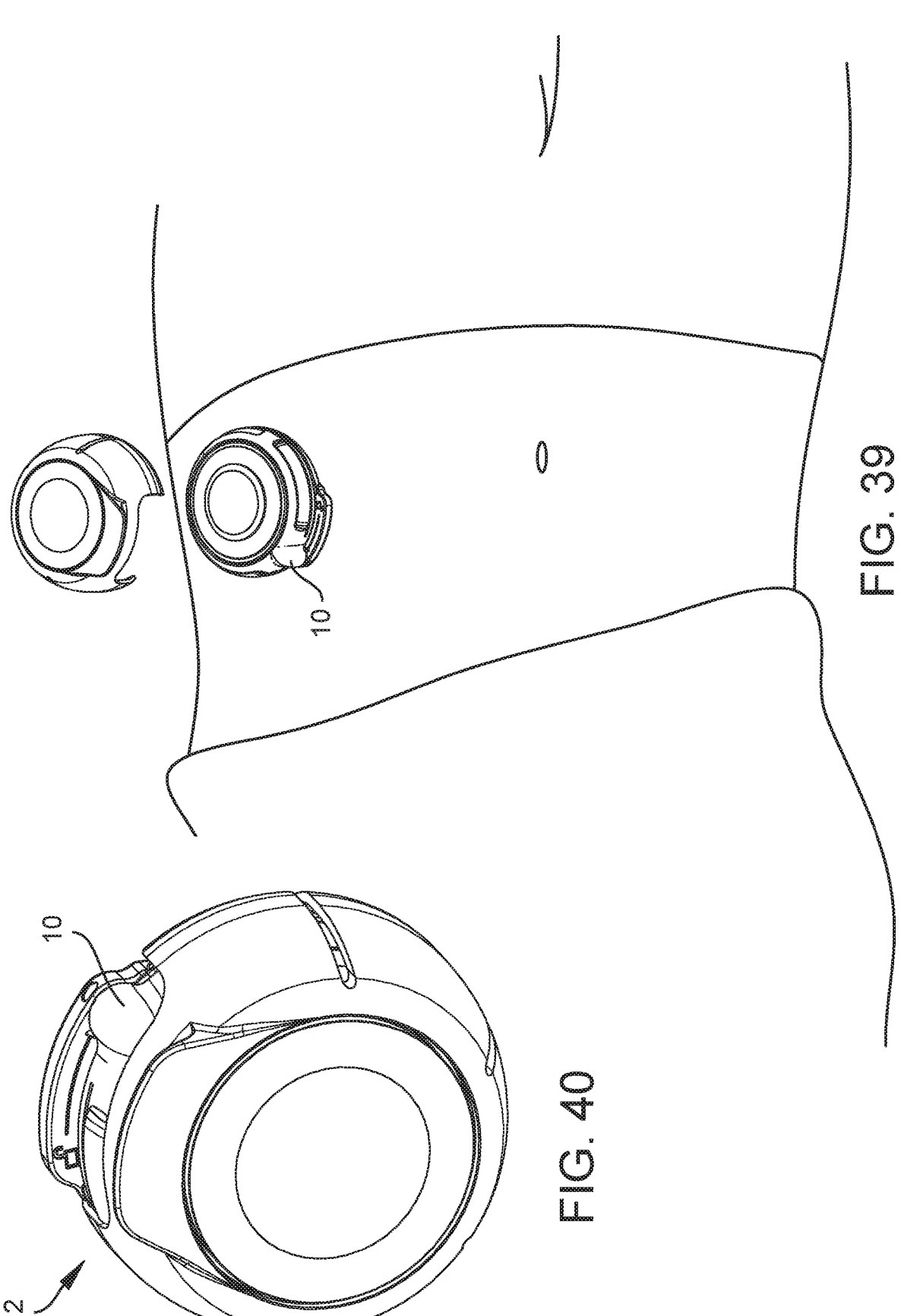
Figures 41, 42, 43, 44, 45:
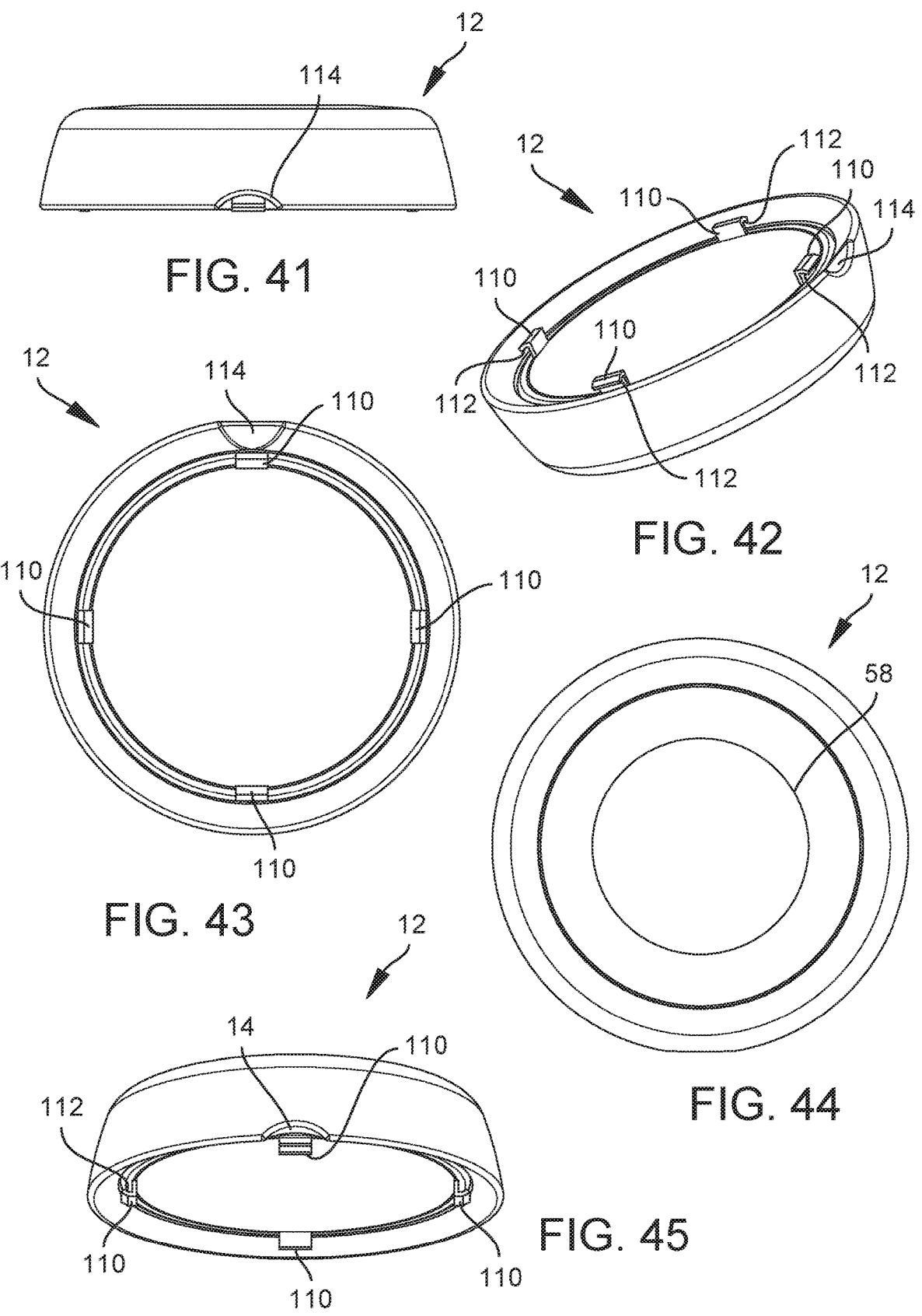
FIGS. 41-47 depict yet another embodiment of a medical device accessory.
Figures 46, 47:
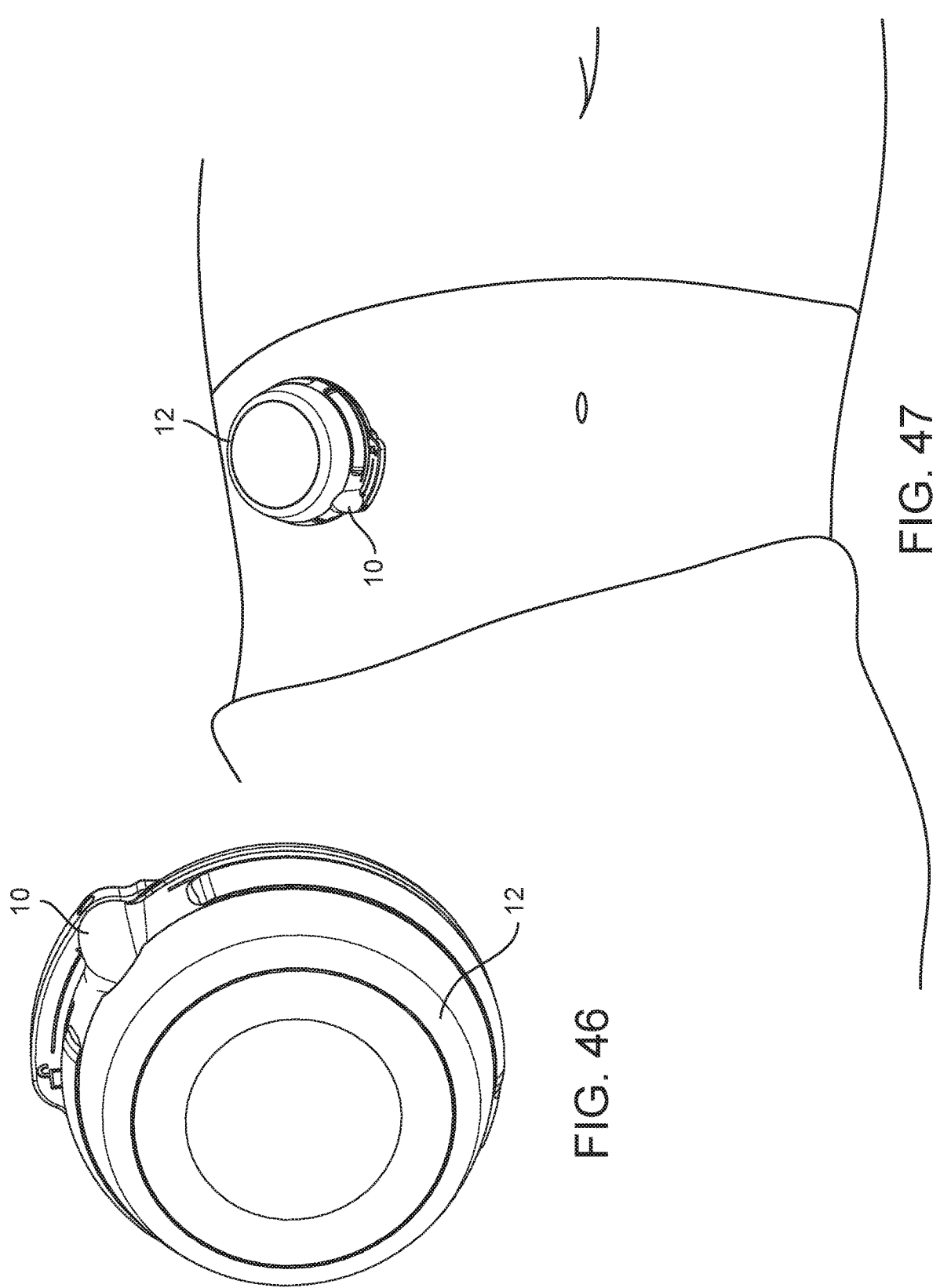
Figures 48, 49, 50, 51:
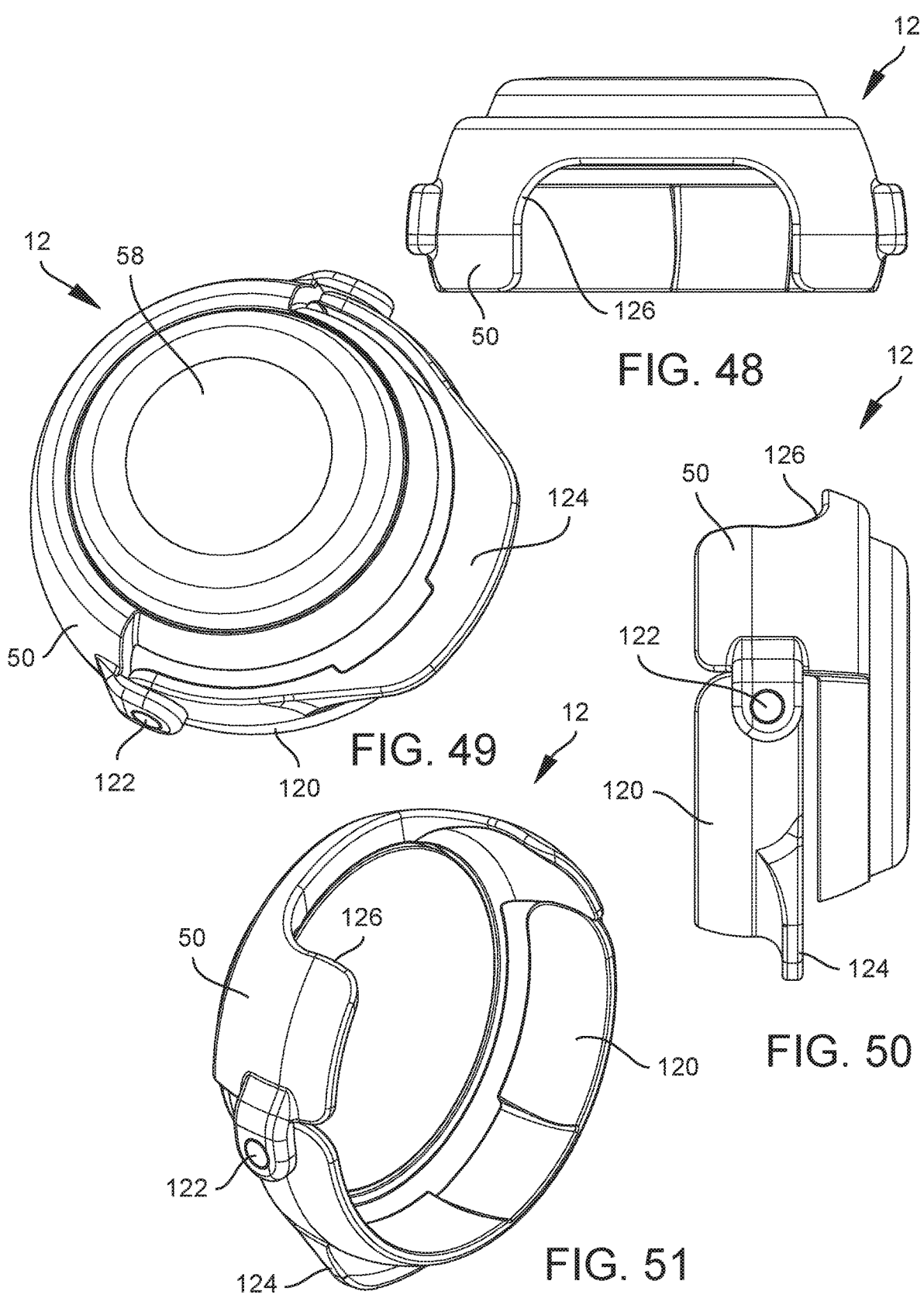
FIGS. 48-51 depict yet another embodiment of a medical device accessory.
Figures 52, 53, 54, 55:
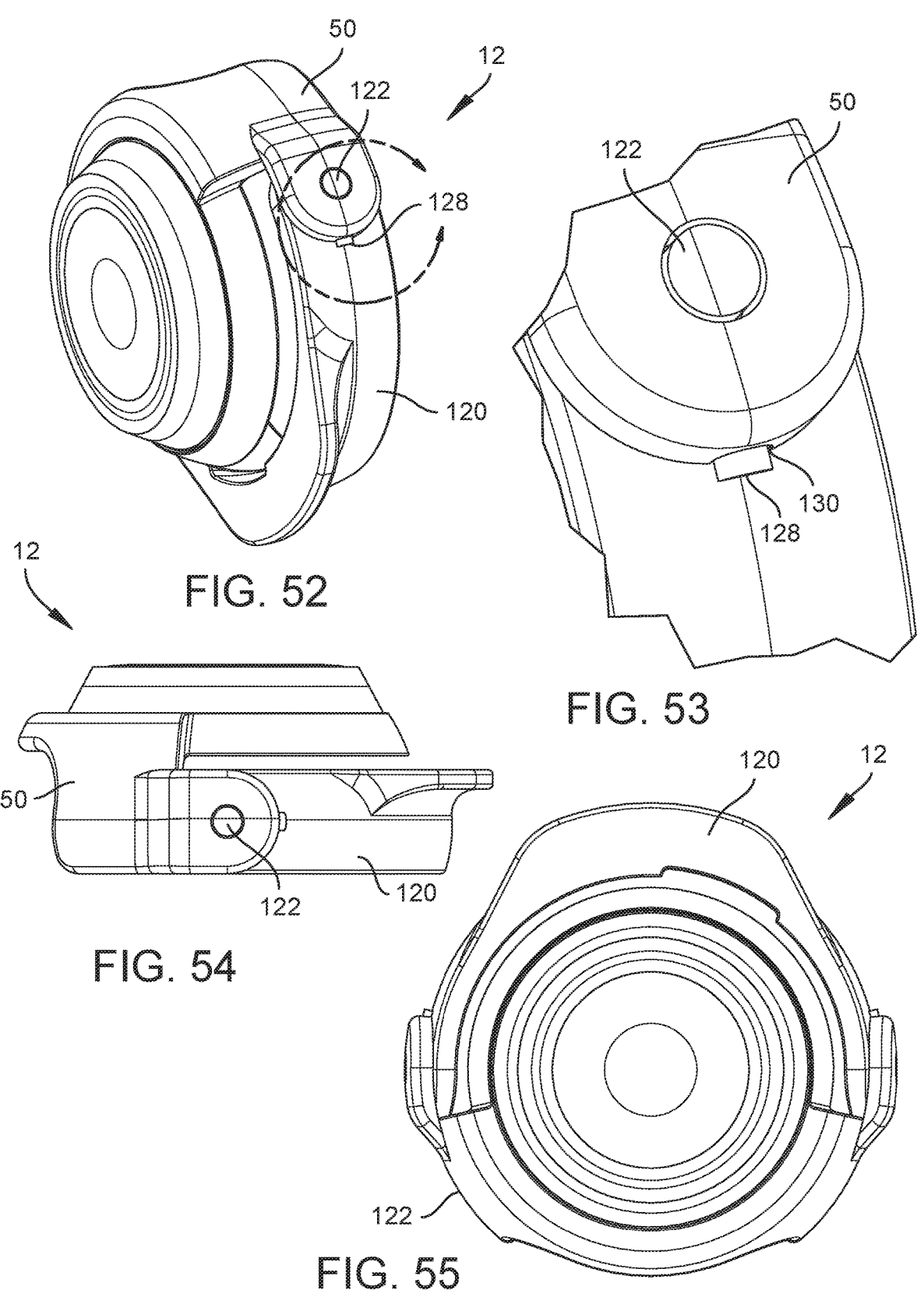
FIGS. 52-55 depict yet another embodiment of a medical device accessory.
Figures 56, 57, 58:
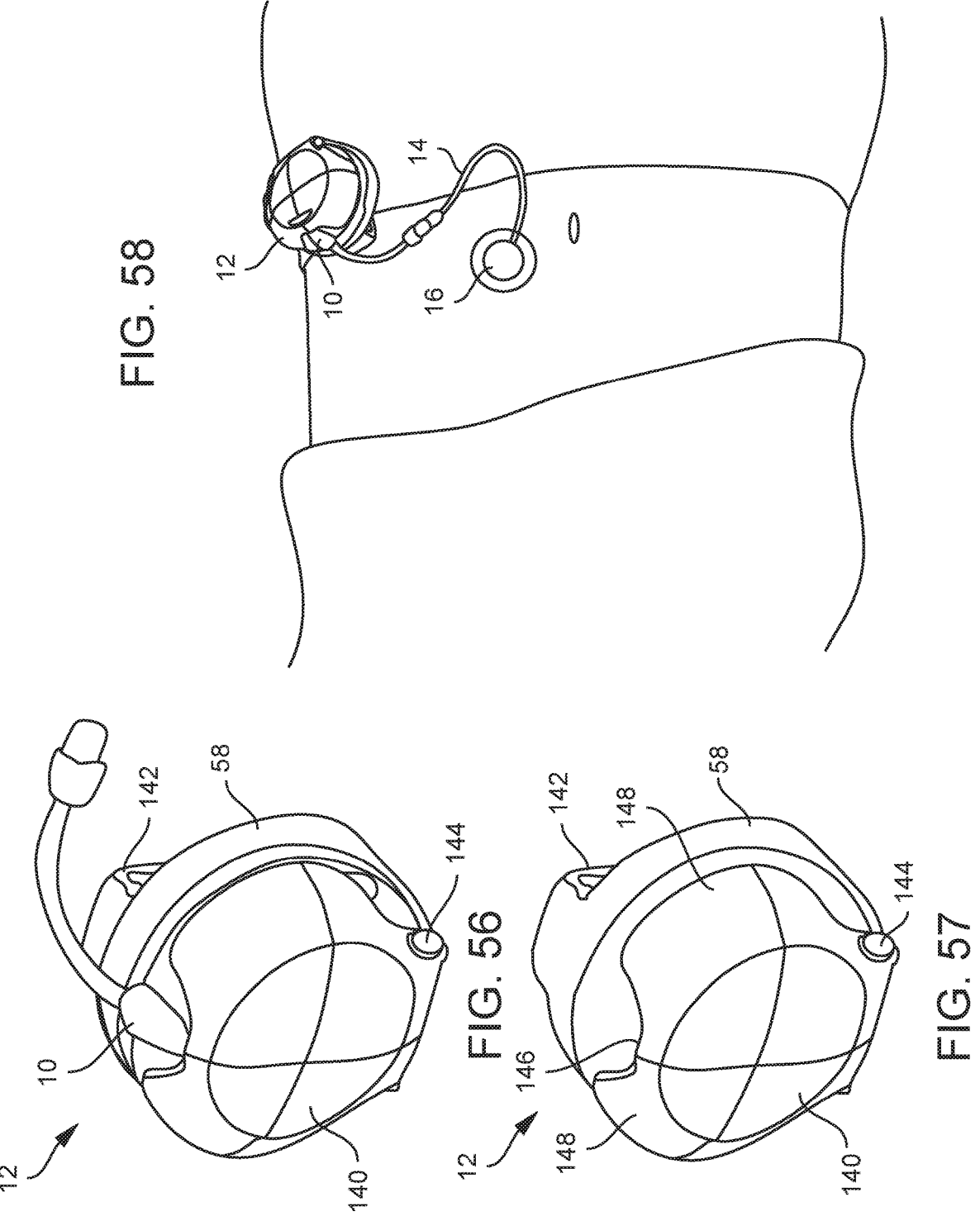
FIGS. 56-58 depict yet another embodiment of a medical device accessory.

The breaks 104 may generate a number of wall segments which are cantilevered to a top portion of the accessory 12. Each segment may act as a coupling member which may help to retain the accessory 12 on a medical device 10. Each cantilevered segment may resiliently deflect outward as the medical device 10 is docked into the cavity 100. A portion of the medical device 10 which is wider than the opening in the bottom of the accessory 12 afforded by the lip 105 when the segments are in the resting state may be passed into the cavity 100 when the segments are deflected outwards. The segments may then restore to a resting state once the medical device 10 is in place within the cavity 100. Thus, the accessory 12 may clip onto the medical device 10 mechanically retaining the accessory 12 in place on the medical device 10. As indicated in FIG. 25, the medical device 10 may remain operating in situ on a patient while the accessory 12 is attached to the medical device 10 by pressing the accessory 12 onto the top of the medical device 10.

The peripheral wall 102 of the accessory 12 may also have a niche 106. The niche 106 may be included to accommodate a protrusion such as a tubing connector or tubing 14 leading from a medical device 10 to a point beyond the footprint of the accessory 12. In the example embodiment, the niche 106 is a cut out having the shape of a Norman window, however, any suitable shape may be used. Additionally, one of the breaks 104 in the peripheral wall 102 extends to the niche 106. This need not be so in all embodiments.

The niche 106 of the example embodiment is flanked on each side by a flange 108. The flanges 108 are included at a bottom of the peripheral wall 102 in the example. The flanges 108 may provide a grasping or contact surface to facilitate removal of the accessory 12 from the medical device 10. The distance the flanges 108 extend from the peripheral wall 102 may vary and in the example increases with proximity to the niche 106.

Referring now to FIG. 27-30 another example accessory is depicted. In this example embodiment, the flange 108 is present along the entirety of the peripheral wall 102 segments adjacent the niche 106. The distance the flanges 108 project from the peripheral wall 102 is variable along a first section and substantially constant along a second section which is proximal the niche 106.

Referring now to FIG. 31-34 in an alternative embodiment, a flange 108 may be included at a top of the accessory 12. Additionally, breaks 104 in the peripheral wall 102 may only be included over a portion of the peripheral wall 102. In the example embodiment, breaks 104 are included at regular angular intervals over the majority of the peripheral wall 102. The niche 106 is flanked on each side by a break 104 free segment of peripheral wall 102.

Referring now to FIGS. 35-40 another embodiment of an accessory 12 including a flange 108 which extends from the top of the accessory 12 is shown. The example embodiments shown in FIGS. 35-38 also includes a peripheral wall 102 having a curvature. This curvature may make the opening in the bottom of the accessory 12 which leads to the cavity 100 smaller than at least a portion of the medical device 10. Thus, as the accessory 12 is coupled onto the medical device 10, the peripheral walls 102 may clip around the medical device 10 to retain the accessory 12 in place. As in other embodiments, the accessory 12 may include a second portion 58 which may include components described in relation to FIGS. 2-8. The accessory 12 also includes a larger niche 106. The larger niche 106 may allow for some rotation of the accessory 12 relative to the medical device 10.

Referring now to FIGS. 41-47 another example embodiment of an accessory 12 is depicted. As shown, the housing 50 of the accessory 12 includes a retention portion including a number of clips 110. The housing 50 also includes a second portion 58 which may include the components described in relation to FIGS. 2-8. A medical device 10 may include a number of receiving recesses for the clips 110 of the accessory 12. In certain examples, this may allow the accessory 12 to mount onto the top of the medical device 10 while the medical device 10 remains operating in situ. In some embodiments, the accessory 12 may be mounted onto the medical device 10 by pressing the accessory 12 against the medical device 10. This may cause each of the clips 110 to deflect around a portion of a respective receiving recess in the medical device 10. As the accessory 12 is further advanced against the medical device 10, the clips 110 may progress past an obstructing portion of the receiving recess and restore back to a resting state. The clips 110 may include a hooked portion 112 which may latch the accessory 12 into place once advanced passed the obstructing portion of the receiving recess. As shown, the housing 50 of the accessory 12 may include an indentation 114. The indentation 114 may be sized to allow a fingertip to reach under the accessory 12 and pry the accessory 12 off of the medical device 10.

In alternative embodiments, the clips 110 of the accessory 12 may interface with a bayonet type mount included in the medical device 10. In such embodiments, the medical device 10 may include an "L" shaped slot for each of the clips 110. The clips 110 of the accessory 12 may be advanced into an opening provided by the leg of the "L" shaped slot. The accessory 12 may then be rotated such that the clips 110 are displaced along the remaining portion of the slots to a region of the slots where removal of the clips 110 from the slot is obstructed. Thus the accessory 12 may be mechanically coupled to the medical device 10. The accessory 12 may be rotated back to a position in which the clips 110 align with the opening provided by the leg of the "L" shaped slot to allow for removal of the accessory 12. In some embodiments, the "L" shaped slot may include a serifed portion in which the clips 110 reside when the accessory 12 is mechanically coupled to the medical device 10. A user may be required to press down on the accessory 12 to advance the clips 110 out of the serifed portion before rotation to remove the accessory 12 from the medical device 10 may be possible.

Referring now to FIGS. 48-51, another example accessory 12 is depicted. As shown, the housing 50 of the accessory 12 includes a retention portion including a pivoting retention member 120. The housing 50 also includes a second portion 58 which may include the components described in relation to FIGS. 2-8. The pivoting retention member 120 shown has an arcuate shape and includes pins 122 included at terminal ends thereof. The pins 122 may extend into bearings included on a remaining portion of the housing 50. During mechanical coupling of the accessory 12 to the medical device 10, the pins 122 may allow the retention member 120 to pivot from a receiving position to a retaining position. In the receiving position, the retention member 120 may be pivoted over the top of the housing 50 allowing the housing 50 to be placed onto the medical device 10 without removing the medical device 10 from a patient. Once in place, the retention member 120 of the accessory 12 may be displaced to the retaining position (shown in FIGS. 48-51). When in the retaining position, the retention member 120 may clip in place around the medical device 10 holding the accessory 12 in place on the medical device 10. The retention member 120 may also include a flange 124. The flange 124 may be included to facilitate grasping and actuation by a user of the accessory 12. The housing 50 also includes a notch 126. The notch 126 may allow access to user interface component of a medical device 10 similarly to the fenestrations 56 described elsewhere herein.

Figures 59, 60:
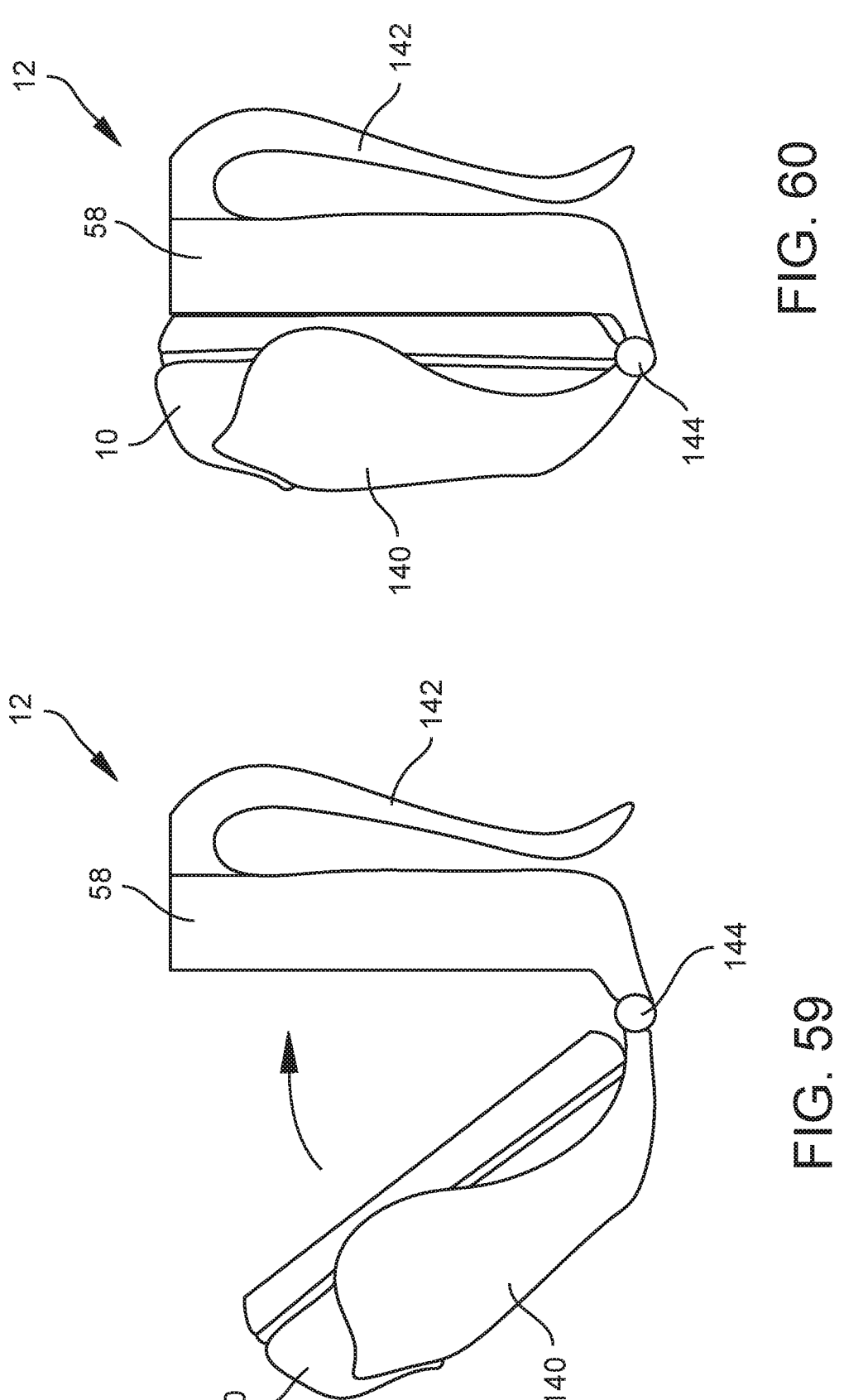
FIG. 59 depicts a medical device accessory in an open state with a medical device installed therein.
FIG. 60 depicts a medical device accessory in a closed state with a medical device installed therein.
Figures 61, 62, 63:
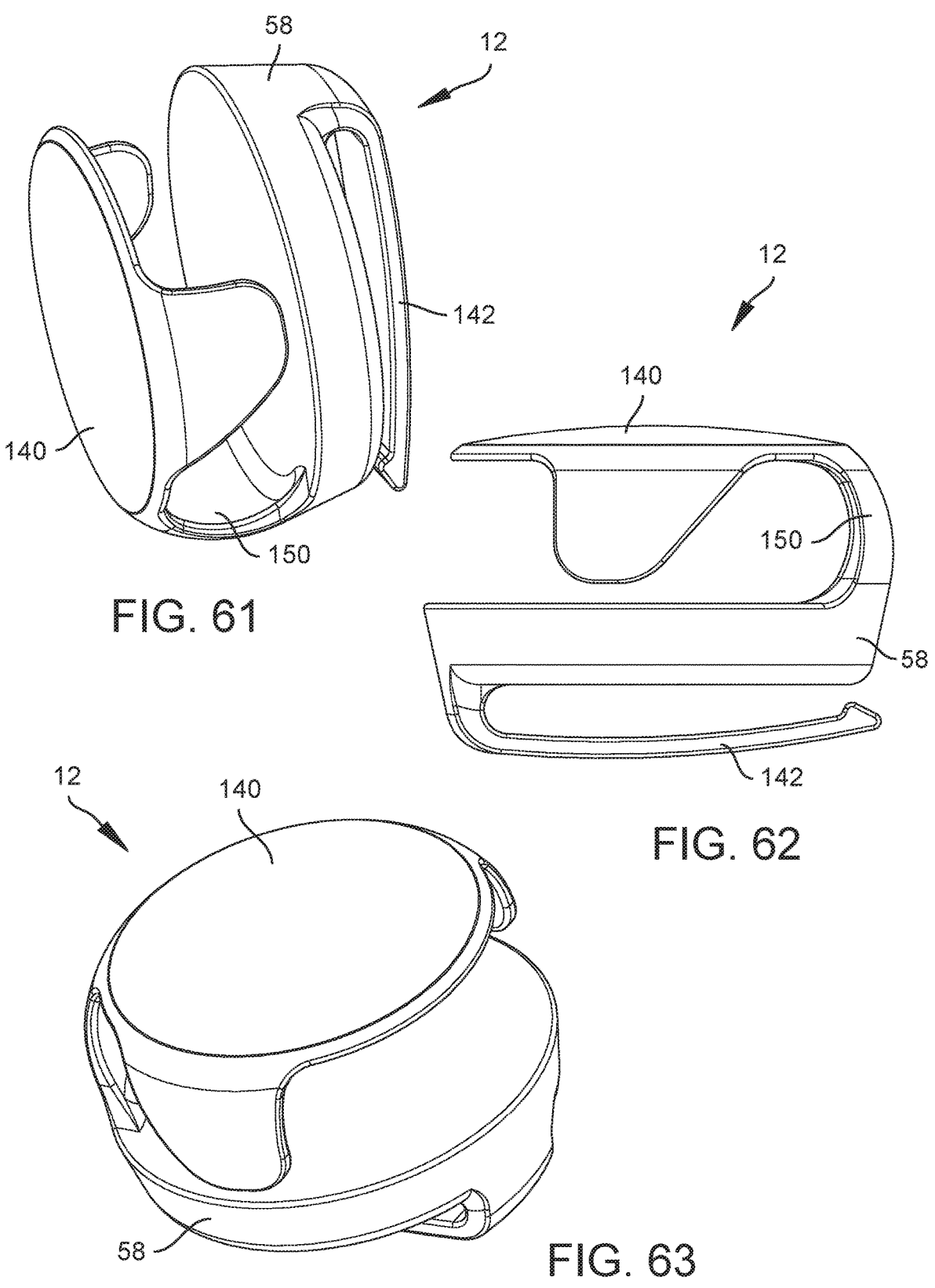
FIGS. 61-65 depict yet another embodiment of a medical device accessory.
Figures 64, 65:
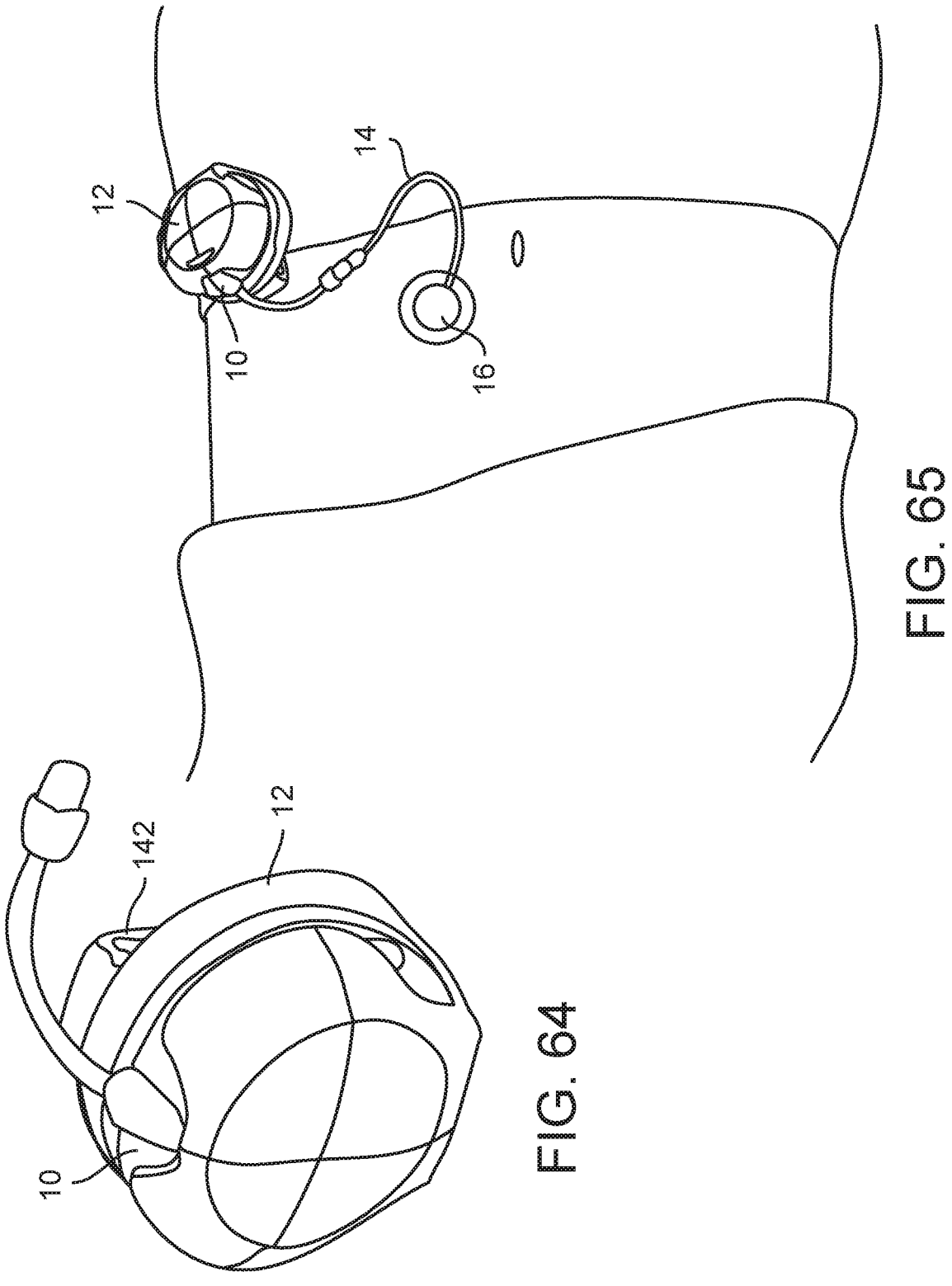
Figures 66, 67, 68, 69:
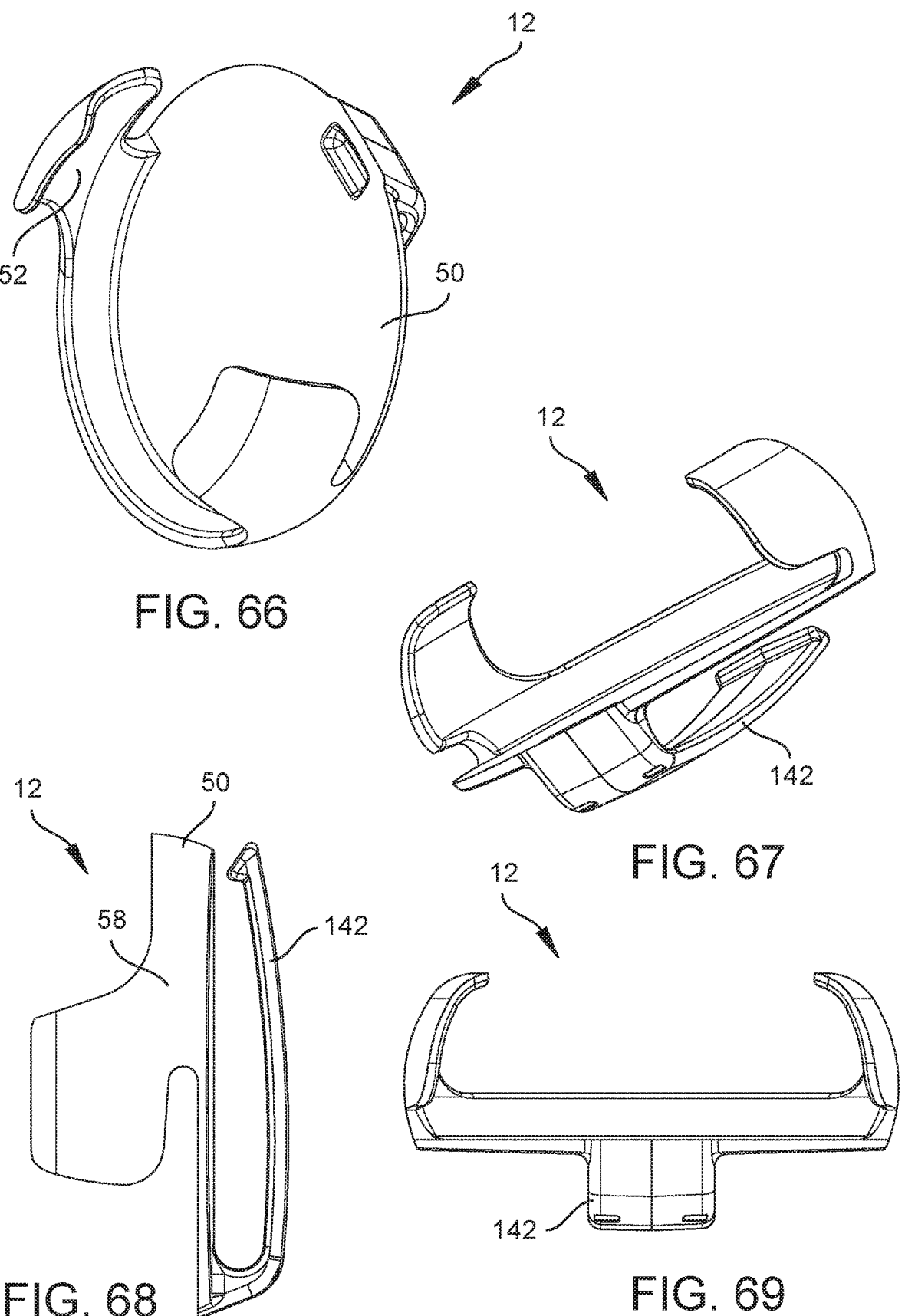
FIGS. 66-69 depict yet another embodiment of a medical device accessory.

Referring now to FIGS. 52-55, another example accessory 12 including a pivotal retention member 120 is shown. The example embodiment depicted in FIGS. 52-55 is configured to latch around the medical device 10 when installed on the medical device 10. As best shown in the detailed view of FIG. 53, the retention member 120 may include a projection 128. When the retention member 120 is in the retaining position, the projection 128 may engage with a detent 130 included on another portion of the housing 50. This may aid in holding the retention member 120 in the retaining position and keep the accessory 12 from being inadvertently removed from the medical device 10 as a user moves about while sleeping for example. Referring now to FIGS. 56-60, another embodiment of an accessory 12 is shown. As shown, the accessory 12 may have a clip 142 which may be disposed on the second portion 58. The second portion 58 may also include the components described in relation to FIGS. 2-8. The second portion 58 may be pivotally coupled to the first portion 140 by a pivot pin 144. The first portion 140 may be pivoted to a loading position in which the medical device 10 may be placed into the accessory 12. From the loading position, the first portion 140 may be pivoted to a retaining position in which the medical device 10 is held in place within the accessory 12. A latching arrangement similar to that shown in FIGS. 52-55 may be included to help hold the first portion 140 in place in the retaining position. The first portion 140 or second portion 58 of the accessory 12 may include a cradle 146 in which the medical device 100 may be installed. As shown in FIG. 59, the medical device 10 is shown in place in a cradle 146 of the first portion 140. The cradle 146 may include one or more wings 148 which may surround at least a portion of the medical device 10 when the medical device 10 is installed in the cradle 146. Once the medical device 10 is positioned in the cradle 146, the first portion 140 of the accessory 12 may be pivoted toward the second portion 58 of the accessory 12. This may sandwich the medical device 10 within the accessory 12 as shown in FIG. 60 for instance. The clip 142 may be attached to a belt or waistband of a user allowing the medical device 10 to operate with the accessory 12 while being carried by the patient.

An alternative embodiment of the accessory 12 shown in FIGS. 56-60 is depicted in FIGS. 61-65. As shown the first portion 140 and second portion 58 are attached to each other via a living hinge 150. Thus, the first portion 140 may be displaced relative to the second portion 58 without the need for a pivot pin 144 (see, e.g. FIGS. 56-60). Additionally, no latching arrangement may be included as the living hinge 150 may be constructed with sufficient resiliency to avoid inadvertent deflection once the medical device 10 has been installed within the accessory 12.

In another alternative embodiment as shown in FIGS. 66-69, an accessory 12 with a housing 50 having a medical device receiver which is shown as a bay 52 that is sized and shaped to receive and retain a medical device 10 or portion thereof. In the example embodiment, the bay 52 includes coupling members which are depicted as arms 54 located on opposing sides of a docking opening in the housing 50. The arms 54 may be contoured to cradle the medical device 10 when the medical device 10 is placed in the accessory 12. As shown, the accessory 12 may include a clip 142 which may be disposed on the second portion 58. The second portion 58 may also include the components described in relation to FIGS. 2-8. The clip 142 may facilitate attachment of the accessory 12 to a belt or waistband of a user. Additionally, the clip 142 may ensure that the arms 54 of the bay 52 are positioned such that the medical device 10 may be holstered in place within the accessory 12 by force of gravity.

Figures 70, 71, 72:
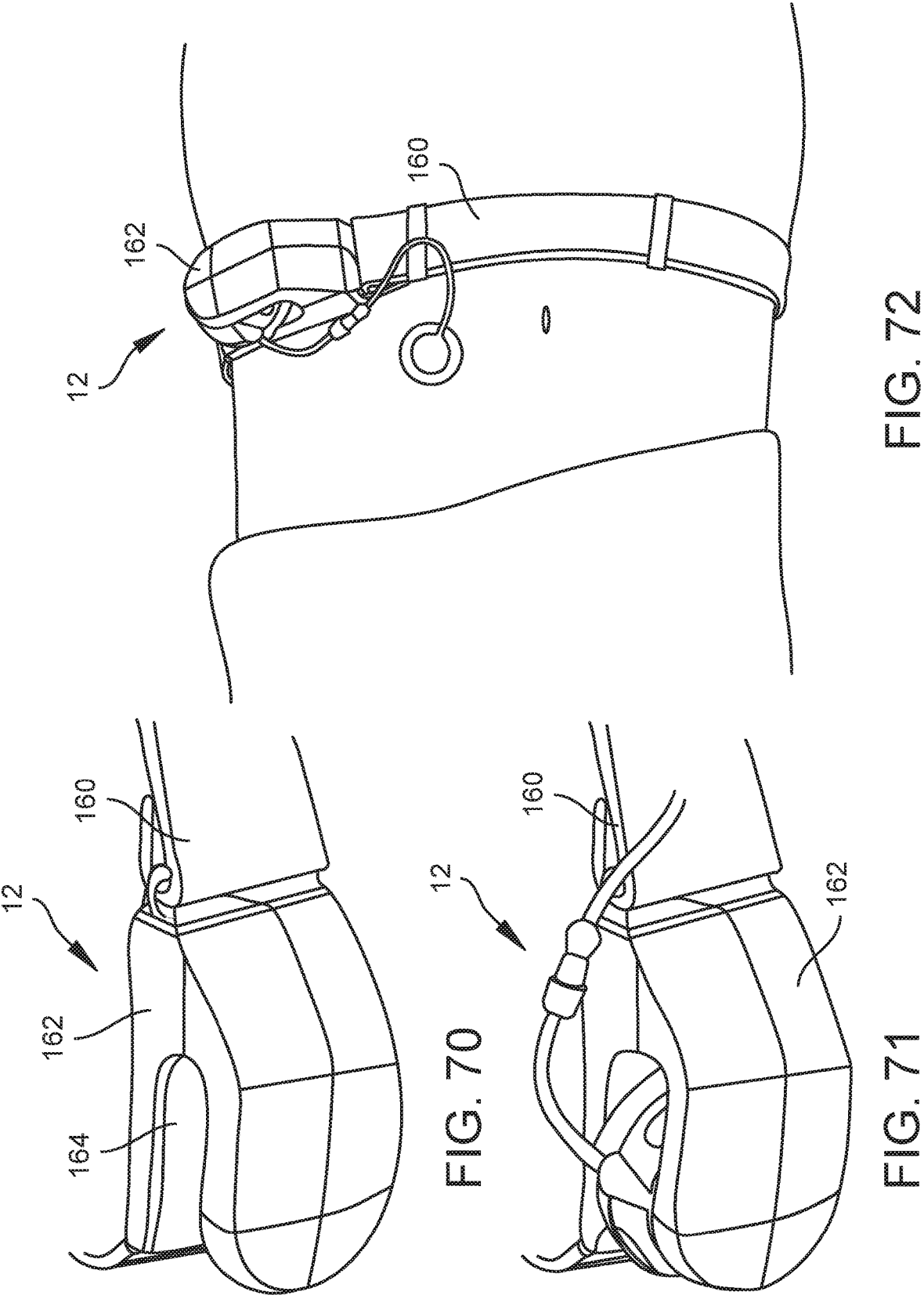
FIGS. 70-72 depict yet another embodiment of a medical device accessory.

In another embodiment and referring now to FIGS. 70-72, the accessory 12 may include a belt 160. Similar components such as strap(s) or slings which facilitate ease of wearing the accessory 12 may be included in various embodiments. As shown, the belt 160 may include a buckle portion 162. The buckle portion 162 may contain one or more of, for example, a battery 24, charging circuitry, a controller (e.g. microprocessor, PLC, FPGA, etc.), memory, alarm 26, and a wireless communicator 28. Additionally, the buckle portion 162 may include a slot 164. The slot 164 may be sized to accept the medical device 10. In some embodiments, the arms 54 such as those depicted in FIGS. 9-12 may be included to aid in retaining the medical device 10 within the slot 164.

Figures 73, 74:
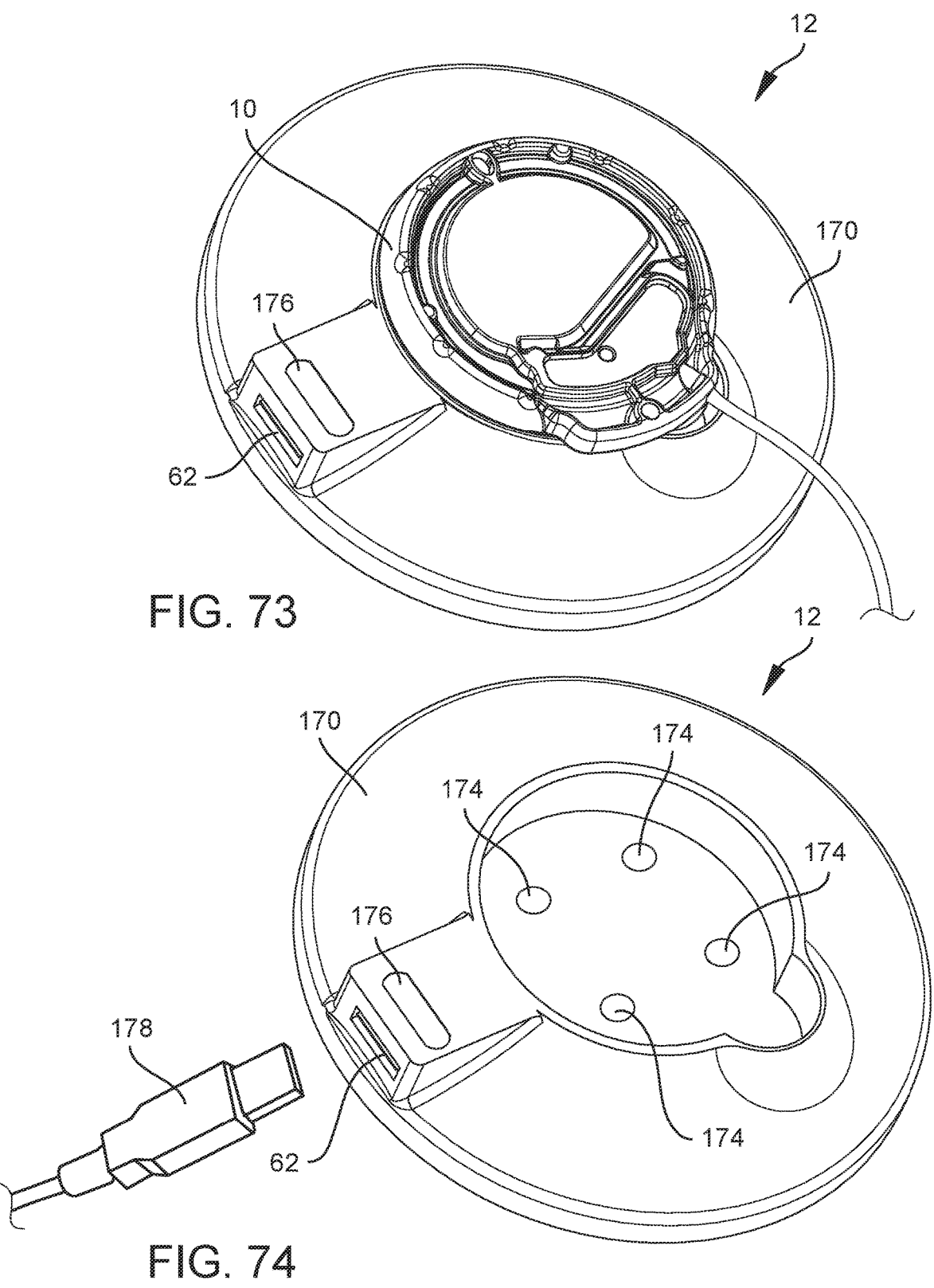
FIGS. 73-74 depict yet another embodiment of a medical device accessory.

Referring now to FIGS. 73-74 another embodiment of an accessory 12 is depicted. As shown, the accessory 12 may include a pad 170 having a depression 172 sized to accept a medical device 10. The depression 172 may include a number of magnets 174 which may couple to magnets included in the medical device 10. Additionally, the pad 170 may contain one or more of, for example, a battery 24, charging circuitry, a controller (e.g. microprocessor, PLC, FPGA, etc.), memory, alarm 26, and a wireless communicator 28. The pad 170 may further include a port 62 which may be used for data (e.g. log transfer or medical device updates) or power communication. A USB type cable 178 is depicted coupled into the port 62 in FIG. 74. An indicator light 176 is included on the pad 170 and may illuminate based on status of the accessory 12 and/or medical device 10. For example, the indicator light 176 may illuminate a first color to indicate that the medical device 10 is being wirelessly charged. The indicator light may blink to indicate a low battery 24 in the accessory 12. The indicator light 176 may illuminate a second color in the event of an alarm encountered by the medical device 10 or accessory 12.

Figures 75, 76:
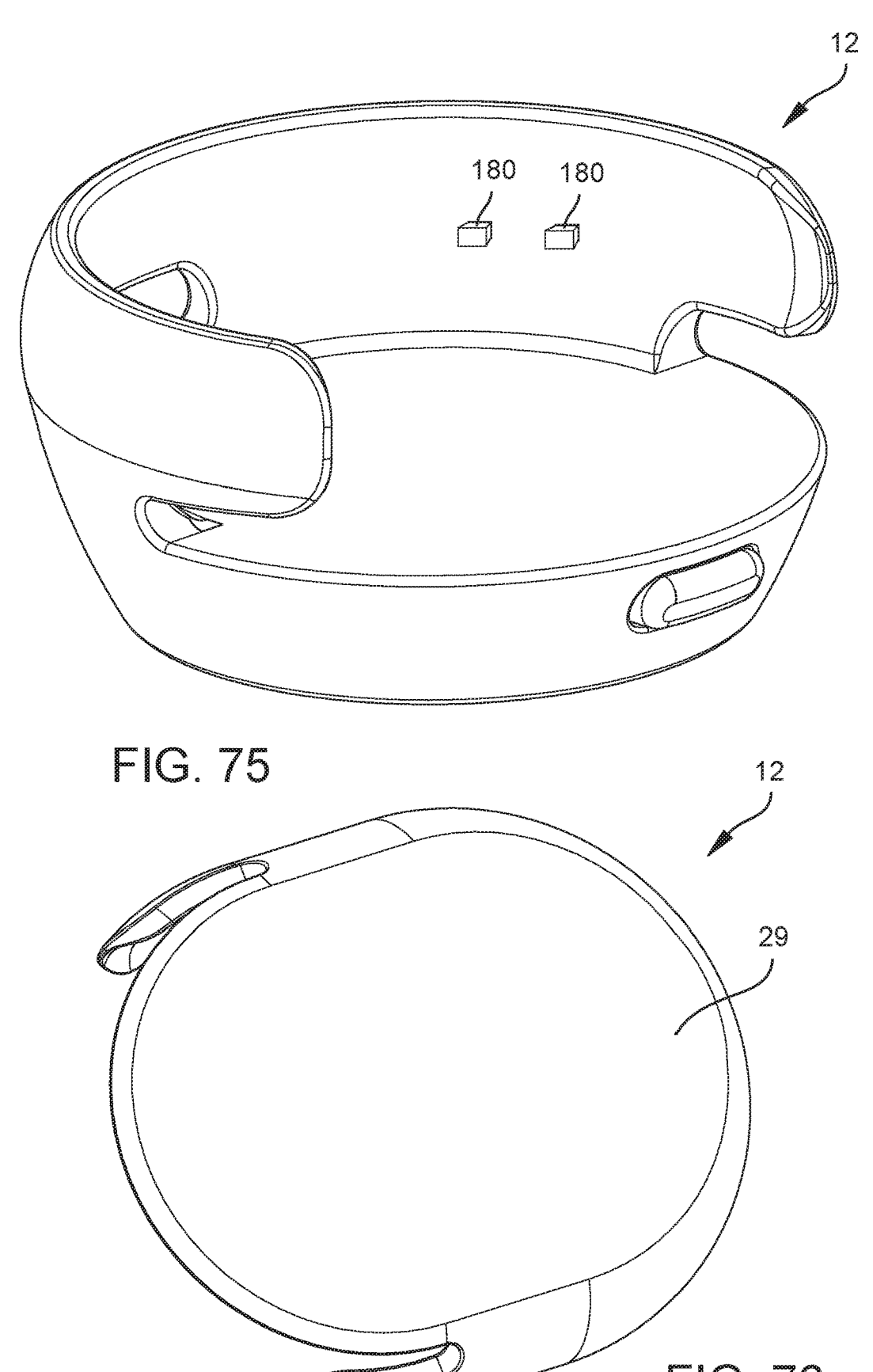
FIG. 75 depicts an embodiment of a medical device accessory having contacts for establishing communication with cooperating contacts on a medical device.
FIG. 76 depicts a medical device accessory having a user interface.
Figure 77:
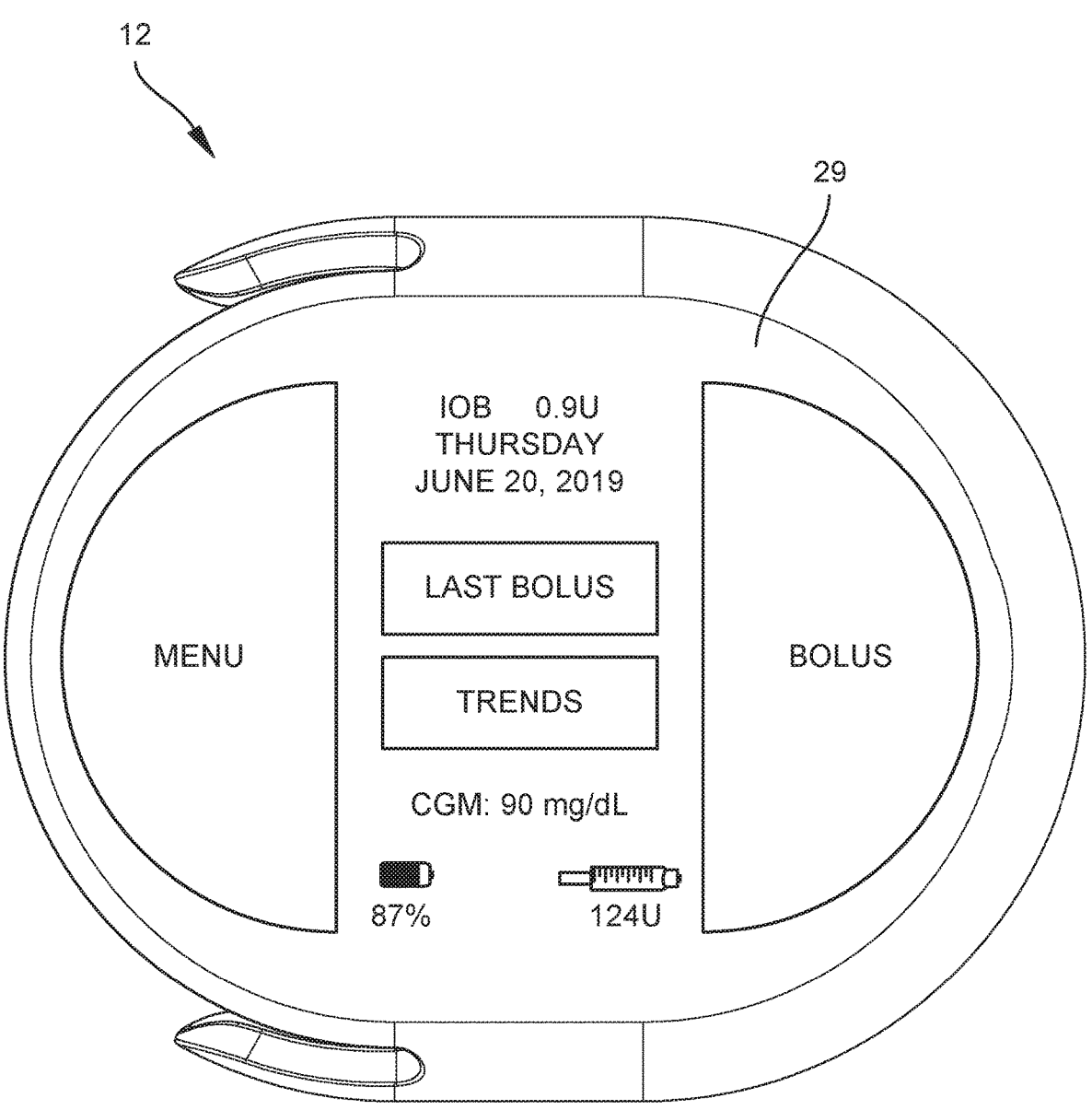
FIG. 77 depicts a medical device accessory having a user interface displaying an exemplary screen.

Referring now to FIG. 75, another exemplary accessory 12 is depicted. The accessory 12 depicted is similar to that shown in FIGS. 2-8, however, the accessory 12 includes a set of conductive contacts 180. When a medical device 10 is placed within the accessory 12, the conductive contacts 180 may interface with conductive zones included on the medical device 10. This may allow for the accessory 12 to interface with the medical device 10 for charging purposes. Referring now to FIGS. 76-77, another example accessory is depicted. As shown, the accessory includes a user interface 29. The user interface 29 may be a touch screen display, though any other suitable type of display may be included. A home screen of the user interface 29 is depicted in FIG. 77. The home screen may include information like a patient's current insulin on board (IOB). The home screen may also include a last reading from a glucose monitor such as a CGM. Other information like the date, a battery remaining indicia, and a medication remaining indicia may be included. The user may also be able to access information about a last bolus or blood glucose trend data from the home screen. A bolus button may be included on the home screen. Additionally, the home screen may include a menu button which may be used to access various settings, program infusion profiles, view historical patient data, access tutorials, etc. The user interface 29 may show any number of other screens allowing a user to program and use the medical device 10. A number of example screens which may be generated for presentation on the user interface 29 are described in greater detail in: U.S. Pat. No. 9,132,227, issued Sep. 15, 2015 and entitled Methods and Systems for Controlling an Infusion Pump; U.S. Pat. No. 9,656,031, issued May 23, 2017 and entitled Infusion Pump Methods and Systems; U.S. Pat. No. 9,662,438, issued May 30, 2017 and entitled Devices, Methods and Systems for Wireless Control of Medical Device; U.S. Pat. No. 10,238,794, issued March 26, 2019 and entitled Devices, Methods and Systems for Wireless Control of Medical Devices; and U.S. Pat. No. 10,195,343, issued Feb. 5, 20109 and entitled Devices, Methods and Systems for Wireless Control of Medical Devices, each of which is incorporated herein by reference in its entirety.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein.

Modifications and substitutions by one of ordinary skill in the art are considered to be within the scope of the present invention.

What is claimed is:

1. A medical device system comprising:

a medical device having first conductive contacts and an adhesive for attaching the medical device to a patient, and comprising a reusable first portion and a disposable second portion attached to the first portion; and an accessory, wherein the accessory configured to attach to the first portion and contact the second portion of the medical device and has second conductive contacts to contact the first conductive contacts and to provide battery power to the medical device as the medical device is attached to the patient.

2. The medical device system of claim 1 wherein the first portion is a pump.

3. The medical device systems of claim 1 wherein the second portion is a reservoir.

4. The medical device systems of claim 2 wherein the second portion is a reservoir.

\* \* \* \* \*